US010064930B2

(12) United States Patent
Hayes et al.

(10) Patent No.: US 10,064,930 B2
(45) Date of Patent: Sep. 4, 2018

(54) IMMUNOGENIC COMPOSITIONS AND METHODS FOR PIGEON FEVER

(71) Applicants: Phillip Wayne Hayes, Maurice, IA (US); Kristina J. Hennessy, Leawood, KS (US)

(72) Inventors: Phillip Wayne Hayes, Maurice, IA (US); Kristina J. Hennessy, Leawood, KS (US)

(73) Assignees: BOEHRINGER-INGELHEIM VERMEDICA, INC.; Kristina J. Hennessy

( * ) Notice: Subject to any disclaimer, the term of this patent is extended or adjusted under 35 U.S.C. 154(b) by 0 days.

(21) Appl. No.: 14/996,532

(22) Filed: Jan. 15, 2016

(65) Prior Publication Data

US 2016/0206722 A1 Jul. 21, 2016

Related U.S. Application Data

(60) Provisional application No. 62/104,260, filed on Jan. 16, 2015.

(51) Int. Cl.
| | | |
|---|---|---|
| *A61K 39/05* | (2006.01) | |
| *A61K 31/7036* | (2006.01) | |
| *A61K 31/7048* | (2006.01) | |
| *A61K 39/00* | (2006.01) | |

(52) U.S. Cl.
CPC .......... *A61K 39/05* (2013.01); *A61K 31/7036* (2013.01); *A61K 31/7048* (2013.01); *A61K 2039/521* (2013.01); *A61K 2039/552* (2013.01); *A61K 2039/55505* (2013.01)

(58) Field of Classification Search
None
See application file for complete search history.

(56) References Cited

U.S. PATENT DOCUMENTS

| | | | | |
|---|---|---|---|---|
| 3,139,382 A | * | 6/1964 | Killinger | A61K 39/02 424/234.1 |
| 6,682,745 B1 | * | 1/2004 | Jacobs | A61K 39/05 424/237.1 |
| 2007/0134269 A1 | * | 6/2007 | Chu | A61K 9/0024 424/202.1 |
| 2012/0237543 A1 | * | 9/2012 | Hayes | C12N 7/00 424/202.1 |

OTHER PUBLICATIONS

Gorman et al. Veterinary Therapeutics. vol. 11, No. 1, Spring 2010, pp. E1-E8.*
Fontaine et al. Vaccine 24 (2006) 5986-5966.*
Maier et al. Chapter 3. Bacterial Growth. Environmental Microbiology. 2000.*
Hodgson et al. Infection and Immunity, Dec. 1994, vol. 62, No. 12, p. 5275-5280.*
Pigeon Fever Guidelines. Obtained from https://aaep.org/sites/default/files/Guidelines/PigeonFeverGuidelines52713.pdf Nov. 7, 2017.*
Stefanska et al., "Evaluation of Three Methods for DNA Fingerprinting of corynebacterium pseudotuberculosis Strains Isolated from Goads in Poland". Polish Journal of Microbiology, vol. 57, No. 2, 2008, pp. 105-112.

* cited by examiner

*Primary Examiner* — Oluwatosin A Ogunbiyi
(74) *Attorney, Agent, or Firm* — Judy Jarecki-Black

(57) ABSTRACT

The disclosure provides for immunogenic compositions against Pigeon Fever, and methods for their use and preparation. The immunogenic compositions, in alternate embodiments, also include other *equine* pathogens.

15 Claims, 7 Drawing Sheets

Specification includes a Sequence Listing.

IMMUNOGENIC COMPOSITIONS AND METHODS FOR PIGEON FEVER

BACKGROUND OF THE INVENTION

Pigeon Fever is also known as Dryland Distemper, Pigeon Breast or Colorado Strangles in horses. Pigeon Fever is endemic to the southwestern United States and has risen dramatically over the past ten years and now affects most areas of the country. The bacterium involved is called *Corynebacterium pseudotuberculosis*. *Corynebacterium pseudotuberculosis* is found in three common species of flies—the housefly, the stable fly and horn fly, which are believed to be the major vectors for the disease. Horn flies, especially, feed on the ventral midline of the horse, which is where many abscesses start. The vector for spreading the disease from horse to horse is a flying insect with a range of about a quarter of a mile. As a result, quarantine is a very inefficient way of trying to limit the spread of this disease.

The basis for the name stems from the behavior of the disease. Pigeon Fever tends to cause abscesses in the chest area of the horse. As the abscess develops the chest swells much like the prominent chest of a pigeon.

Pigeon fever is an *equine* disease that can cause external or internal abscesses and/or an infection or ulcerative lymphangitis in the limbs. Abscesses may form between the jaw bones and in males, in the sheath. It can also affect the mammary area in a mare. The disease starts with a firm diffuse swelling over the affected region. The hard swelling enlarges and then softens like a water balloon as the abscess comes to a head.

Veterinary treatment usually consists of hot packing the swelling until an abscess has formed and is ready to lance. Once the abscess is lanced the open wound is cleaned daily and the affected horse is put on antibiotics for an extended period of time. The problem with Pigeon fever is that it can cause multiple abscesses in a given horse. Frequently horses will have a recurrence once the antibiotics are stopped. In rare cases a horse may even get an internal abscess which can result in peritonitis when it breaks open. The risk in administering antibiotics at first signs of the disease is that internal abscesses may form. It is for this reason that most cases require waiting until the abscess has formed and been lanced before instituting antibiotic treatment.

There is no vaccination for Pigeon Fever. The disease follows a pattern of having one or two years when many horses in an area will get the disease. Then several years will follow without any cases being seen. Because it is spread by flies, on a given ranch if one horse becomes affected, it is likely that a small number of additional cases will be seen. As a result, horses are either susceptible to the disease, or they have immunity as a result of natural exposure earlier in life. Unfortunately, the immunity which a horse develops from contracting Pigeon Fever does not last a lifetime. Horses will sometimes develop the disease more than once in their lives.

A need exists for methods and medicaments for preventing Pigeon Fever or for reducing the incidence or lessening the severity of clinical symptoms associated with such disease, including those associated with *Corynebacterium pseudotuberculosis* bacteria.

BRIEF SUMMARY OF THE INVENTION

The inventors have determined immunogenic compositions comprising one or more isolates of inactivated or live, attenuated *Corynebacterium Pseudotuberculosis* Bacterin-Toxoid, which when live and active and unattenuated are virulent (i.e., at least 50%, 60%, 70%, 80%, 90% or even 100% of seronegative horses, when purposely exposed to *Corynebacterium Pseudotuberculosis*, present with observable abscesses. "Seronegative horses" means naïve horses or horses never exposed to *Corynebacterium pseudotuberculosis*, The isolates of inactivated or live, attenuated *Corynebacterium pseudotuberculosis* can be grown to high titers in culture to yield a vaccine that is able to induce high titers of serum antibodies against *Corynebacterium Pseudotuberculosis* when administered, for example, to an *equine*, for example resulting in a serum optical density by ELISA of at least 0.5, and preferably, at least 1.0, 1.5, 2.0 or 2.5 at a 1:80 dilution of sera. In addition, the isolates grow well in culture and are highly efficient to produce, for example, to a titer of at least $10^6$ CFU/mL, more preferably at least $10^7$ CFU/mL, $10^8$ CFU/mL, $10^9$ CFU/mL, $10^{10}$ CFU/mL or $10^{11}$ CFU/mL. *Corynebacterium Pseudotuberculosis* Bacterin-Toxoid compositions, and combinations thereof, are capable of reducing the duration, severity, and incidence of Pigeon Fever in an animal such as a horse that has been immunized with the compositions and subsequently challenged.

Accordingly, the present invention provides an immunogenic composition comprising one or more isolates of inactivated or live, attenuated *Corynebacterium Pseudotuberculosis* Bacterin-Toxoid, wherein the *Corynebacterium Pseudotuberculosis* Bacterin-Toxoid, prior to inactivation or attenuation, causes detectable disease in at least 50% of seronegative horses exposed to the isolate, or grows in cell culture to $10^6$ CFU/mL or higher, or, when used as a vaccine in equines at a dose of $10^6$ CFU or higher results in a serum ELISA optical density of at least 0.5 at a 1:80 dilution of sera.

In certain embodiments, the isolate, when alive and unattenuated, causes detectable abscesses in at least 50%, 60%, 70%, 80%, 90% or even 100% of seronegative horses upon exposure to the isolate.

The isolate can be grown in cell culture to a titer of at least $10^6$ CFU/mL, more preferably $10^7$ CFU/mL, $10^8$ CFU/mL, $10^9$ CFU/mL, $10^{10}$ CFU/mL and $10^{11}$ CFU/mL. Administration of an immunogenic composition containing the isolate results in a serum ELISA titer of at least 0.5 and preferably at least 1.0, 1.5, 2.0 or 2.5 when tested at a 1:80 dilution of sera.

In the immunogenic compositions of the invention, the one or more isolates of *Corynebacterium Pseudotuberculosis* Bacterin-Toxoid comprise 95% sequence identity with ATCC Accession No. PTA-121358, deposited under the Budapest Treaty at the American Type Culture Collection (P.O. Box 1549 Manassas, Va. 20108 USA) on Jun. 25, 2014. In addition, the immunogenic compositions of the invention contain at least a *Corynebacterium Pseudotuberculosis* Bacterin-Toxoid isolate, when not inactivated, is active to infect and replicate in host animals.

In addition, the invention further includes multivalent immunogenic compositions comprising inactivated or live attenuated viruses, bacteria, or antigens from pathogens other than *Corynebacterium Pseudotuberculosis* Bacterin-Toxoid that cause disease in Equidae. In particular, the invention provides immunogenic compositions comprising, in addition to inactivated or live, attenuated *Corynebacterium Pseudotuberculosis* Bacterin-Toxoid, at least one antigen or one inactivated or live, attenuated isolate of *Equine* Herpes Virus (EHV), and, in particular embodiments, the EHV is selected from the group consisting of EHV-1 and EHV-4, and a combination thereof, more specifically, the *Equine* Herpes Virus is selected from the group consisting of EHV-1, EHV-4, isolates deposited with the ATCC under accession Nos. PTA-9525 and PTA-9526, and a combination thereof.

The immunogenic compositions of the invention may include, in addition to inactivated or live, attenuated *Corynebacterium Pseudotuberculosis* Bacterin-Toxoid, at least one inactivated or live, attenuated virus or at least one antigen of one or more isolates selected from the group consisting of *Equine* Herpes Virus types 1 and 4, *Equine* Influenza Virus (EIV) West Nile Virus, Eastern *Equine Encephalomyelitis* Virus, Western *Equine Encephalomyelitis* Virus, Venezuelan *Equine Encephalomyelitis* Virus, and Tetanus Toxoid, and combinations thereof. Alternatively, the immunogenic composition, in addition to inactivated or live, attenuated *Corynebacterium Pseudotuberculosis* Bacterin-Toxoid, comprises one or more inactivated or live, attenuated isolates of or antigens of isolates of Eastern *Equine Encephalomyelitis*, Western *Equine Encephalomyelitis*, Venezuelan *Equine Encephalomyelitis* Virus, and Tetanus Toxoid. In specific embodiments, the *Equine* Influenza Virus is selected from the group consisting of Clade 1 viruses, Clade 2 viruses, Influenza A/South Africa/2003, Influenza A/*equine*-2/Ohio/03, Influenza A/*equine*-2/New Market/2/93, Influenza A/*equine*-2/Kentucky/95, Influenza A/*equine*-2/Richmond/1/2007, isolates deposited with the ATCC under accession Nos. PTA-9522, PTA-9523, and PTA-9524, and combinations thereof. The West Nile Virus is one of the isolates selected from the group consisting of Horse Origin 2005, deposited with the ATCC under accession number PTA-9409; NAEE159, deposited at the United States Department of Agriculture Isolate under accession number 405330; NY2002Nassau; NY2002Clinton; NY2002Queens; GA20021; GA20022; TX20021; TX20022; IN2002; NY2003Albany; NY2003Suffolk; NY2003Chatauqua; CO20031; CO20032; TX2003; TX2003Harris4; TX2003Harris6; TX2003Harris7; TX2003Harris10; AZ2004; and TX2004Harris4; and combination thereof. In immunogenic compositions comprising Western *Equine Encephalomyelitis* Virus, the isolate may be the isolate deposited with the ATCC under accession number PTA-9410. In compositions comprising Venezuelan *Equine Encephalomyelitis* Virus, the isolate may be the isolate deposited with the ATCC under accession number PTA-9411. In immunogenic compositions comprising Eastern *Equine Encephalomyelitis* Virus, the isolate may be the isolate deposited with the ATCC under accession number PTA-9412. And, in immunogenic compositions comprising *Equine* Herpes Virus, the isolate may be selected from the group consisting of the isolates deposited with the ATCC under accession Nos. PTA-9525 or PTA-9526, and combinations thereof. In particular, the one or more isolates of *Equine* Rhinitis Virus Type A (ERAV) or *Equine* Rhinitis Virus Type B (ERBV) preferably include ERAV/ON/05 (ATCC Accession No. PTA-11828) and/or ERBV isolate 07-103042 (ATCC Accession PTA-11829) or may comprise genomic sequences in accordance with US Pub. No. 2012-0237543 A1, hereby incorporated by reference in its entirety.

In specific embodiments, one or more of the isolates in the immunogenic composition are present in an amount from about $10^{2.0}$ CFU/mL to about $10^{10.0}$ CFU/mL per dose. The composition may further include a suitable pharmaceutical carrier, such as a diluent, adjuvant, antimicrobial agent, preservative, inactivating agent, or combination thereof. In particular embodiments, the immunogenic composition comprises an adjuvant, specifically, a carbomer.

The invention further provides methods for reducing the incidence or lessening the severity of clinical symptoms associated with or caused by *Corynebacterium Pseudotuberculosis* in an animal or a herd of animals comprising the step of administering an immunogenic composition that comprises one or more isolates of inactivated or live, attenuated *Corynebacterium Pseudotuberculosis* Bacterin-Toxoid isolates, prior to inactivation or attenuation, causes detectable clinical signs of disease in at least 50% of seronegative horses exposed to the isolate, or grows in cell culture to $10^6$ CFU/mL or higher, or, when used as a vaccine in equines at a dose of $10^6$ CFU or higher results in a serum ELISA optical density titer of at least 0.5 at a sera dilution of 1:80.

In addition to providing methods for reducing the incidence or lessening the severity of clinical symptoms associated with or caused by Pigeon Fever or *Corynebacterium Pseudotuberculosis* in an animal or a herd of animals, the methods of the invention may further reduce the incidence or lessening the severity of clinical symptoms associated with or caused by one or more of the pathogens selected from the group consisting of West Nile Virus, Eastern *Equine Encephalomyelitis* Virus, Western *Equine Encephalomyelitis* Virus, Venezuelan *Equine Encephalomyelitis* Virus, *Clostridium tetani*, EHV-1, EHV4, ERAV, ERBV and combinations thereof in an animal or a herd of animals by administering an immunogenic composition of the invention.

In connection with the methods of the invention, the incidence of clinical symptoms caused by one or more of said pathogens in a herd of animals is reduced from about 10%-50% as compared to a herd not receiving the immunogenic composition. The methods of the invention, in particular embodiments, provide a duration of immunity of at least 6 months against one or more of the pathogens present in the immunogenic composition. In the methods of the invention, the immunogenic composition is administered to an Equidae, preferably a horse. The dosing scheme may include administration of the immunogenic composition in one or more doses. The doses for the methods of the invention may be formulated in 0.5 mL to 2.5 mL dosage forms. Preferably, the methods of the invention administer immunogenic compositions which are safe for use in foals or horses 4 months of age or older.

The invention also provides methods for producing an immunogenic composition comprising one or more isolates of inactivated *Corynebacterium Pseudotuberculosis* Bacterin-Toxoid as follows:
a) growing the virulent *Corynebacterium pseudotuberculosis* organism in growth media which allows high CFU/mL titer and high Phospholipase D production by the organism Toxoid;
b) harvesting the bacteria, phospholipase D and media;
c) contacting the bacteria, phospholipase D, and media with an inactivating agent to obtain the inactivated *Corynebacterium Pseudotuberculosis* Bacterin-Toxoid, and;
d) filtering the media to yield a purified *Corynebacterium Pseudotuberculosis* organism and phospholipase D toxoid.

DETAILED DESCRIPTION OF THE INVENTION

Figure 1:
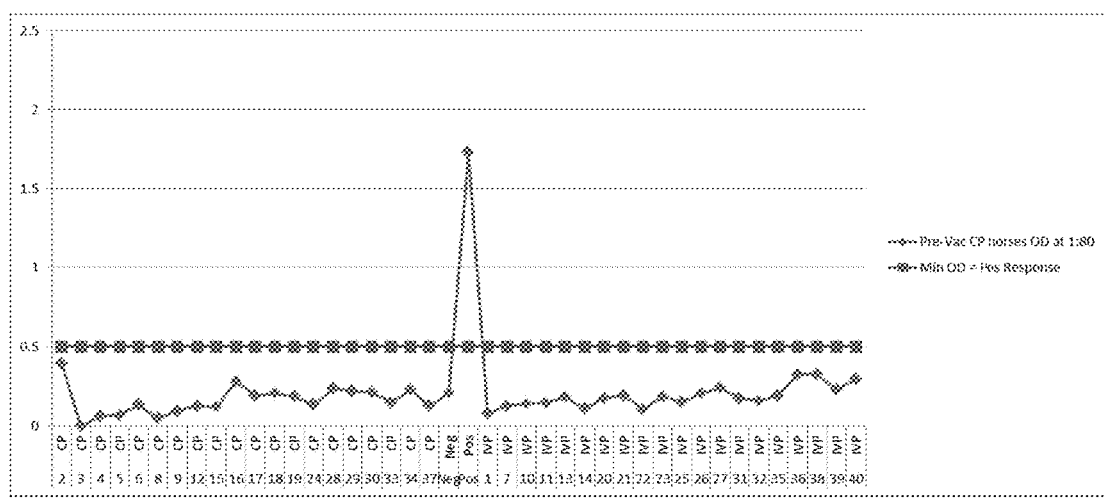
FIG. 1 is a graphical representation of Day 0 Pre-Vaccination Optical Density (OD) Evaluation of Horse Sera Obtained by ELISA Evaluation.
Figure 2:
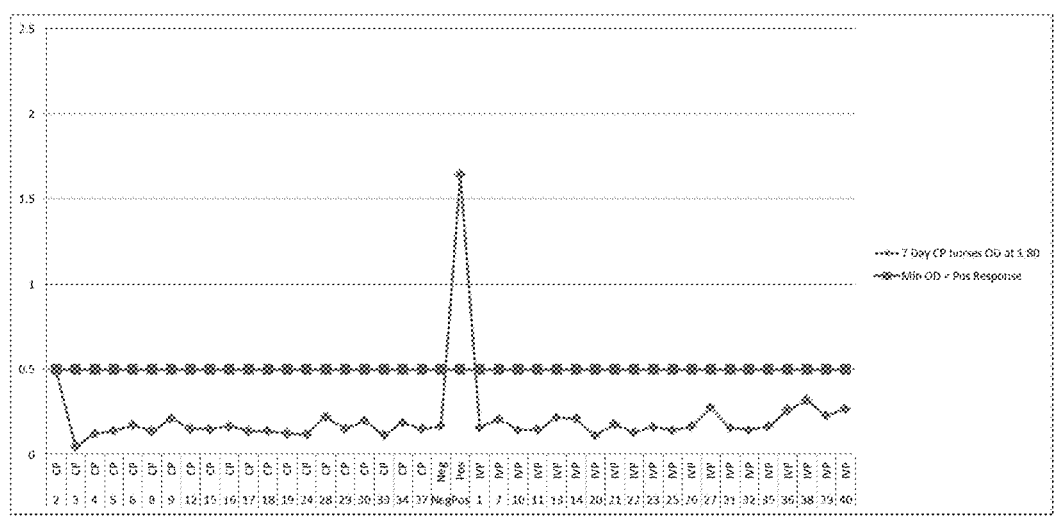
FIG. 2 is a graphical representation of Day 0 Pre-Vaccination Optical Density (OD) Evaluation of Horse Sera Obtained by ELISA Evaluation.
Figure 3:
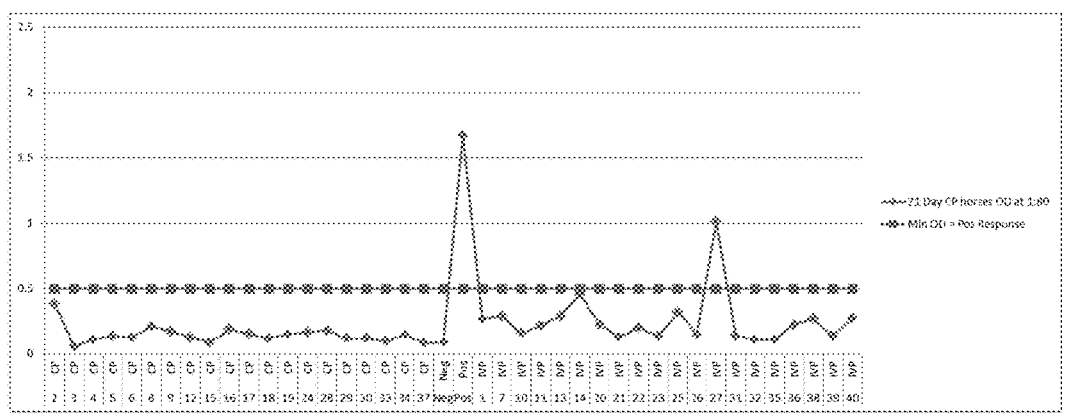
FIG. 3 is a graphical representation of Day 21 (Day of $2^{nd}$ Vaccination) Optical Density (OD) Evaluation of Horse Sera Obtained by ELISA Evaluation.
Figure 4:
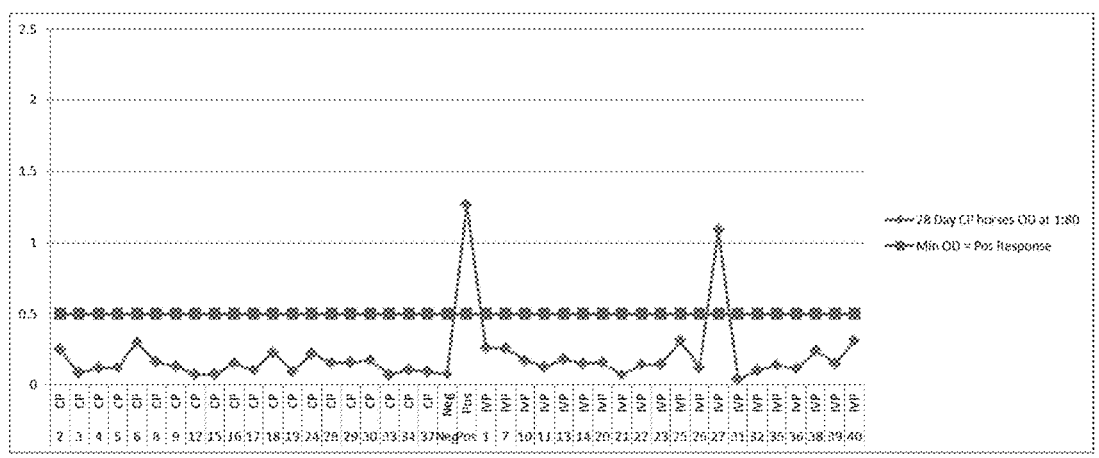
FIG. 4 is a graphical representation of Day 28 Optical Density (OD) Evaluation of Horse Sera Obtained by ELISA Evaluation.
Figure 5:
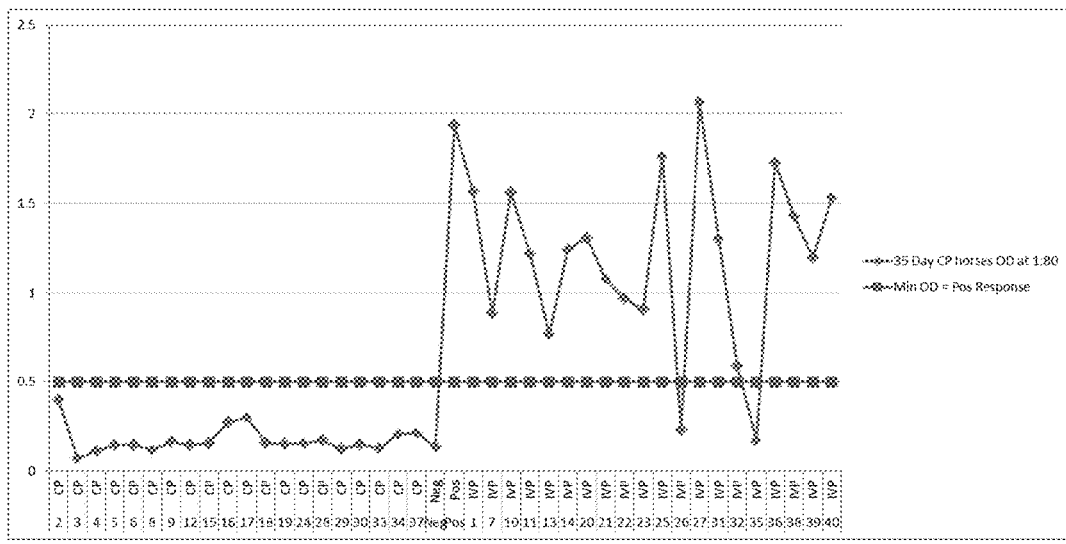
FIG. 5 is a graphical representation of Day 35 Optical Density (OD) Evaluation of Horse Sera Obtained by ELISA Evaluation.
Figure 6:
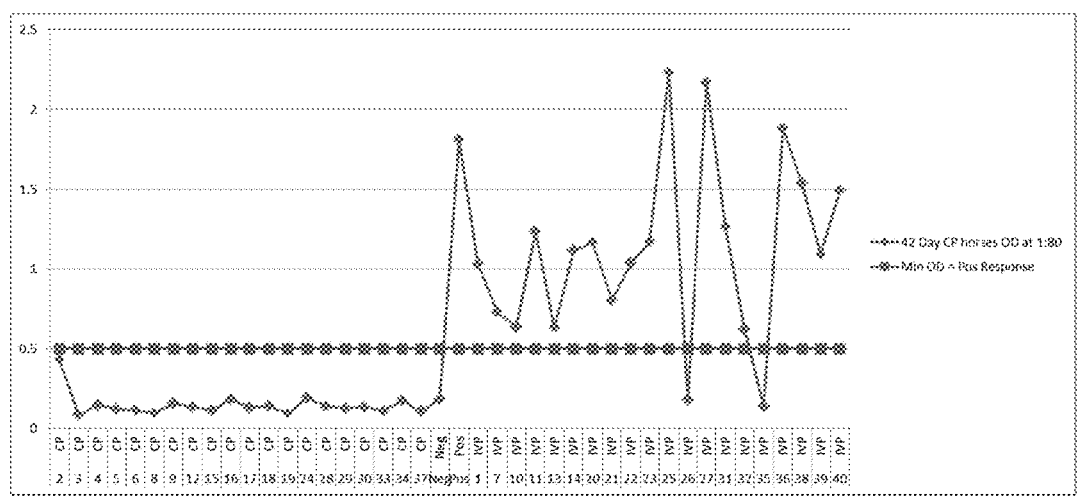
FIG. 6 is a graphical representation of Day 42 Optical Density (OD) Evaluation of Horse Sera Obtained by ELISA Evaluation.

The inventors have determined that immunogenic compositions comprising one or more isolates of inactivated *Corynebacterium Pseudotuberculosis* Bacterin-Toxoid, which when live and active are virulent (i.e., at least 50%, 60%, 70%, 80%, 90% or even 100% of seronegative horses, when purposely exposed to the virus, present with observable abscesses), may be grown to high titers in culture to yield a vaccine that is able to induce high titers of serum antibodies against *Corynebacterium pseudotuberculosis* when administered, for example, to an *equine*, for example resulting in a serum ELISA optical density of at least 0.5, and preferably, at least 1.0, 1.5, 2.0 or 2.5. In addition, the isolates grow well in culture and are highly efficient to produce, for example, to a titer of at least $10^6$ CFU/mL, more preferably $10^7$ CFU/mL, $10^8$ CFU/mL, $10^9$ CFU/mL, $10^{10}$ CFU/mL or $10^{11}$ CFU/mL. The *Corynebacterium pseudotuberculosis* compositions of the present invention are capable of reducing the duration, severity, and incidence of disease in an animal such as a horse that has been immunized with the compositions and subsequently challenged.

In one embodiment, an immunogenic composition comprising one or more isolates of inactivated *Corynebacterium Pseudotuberculosis* Bacterin-Toxoid. Alternatively, the isolates may be attenuated by routine means and the live, attenuated bacterium used in the vaccine composition In some embodiments, the *Corynebacterium Pseudotuberculosis* Bacterin-Toxoid isolate CPS-002+1 05-13-13, having ATCC Accession No: PTA-121358, deposited with the American Type Culture Collection on Jun. 25, 2014, which is hereby incorporated by reference.

In other embodiments, immunogenic compositions provided herein further comprise at least one antigen or one additional inactivated or live, attenuated isolate of *Equine* Herpes Virus (EHV). In some embodiments the compositions comprise at least one antigen of EHV. In some embodiments the EHV is selected from the group consisting of EHV-1, EHV-4, isolates deposited with the ATCC under accession Nos. PTA-9525 and PTA-9526, and combinations thereof.

In one embodiment, along with the inactivated (or attenuated) one or more isolates of *Corynebacterium Pseudotuberculosis* Bacterin-Toxoid, the immunogenic compositions provided herein further comprise at least one antigen or one additional inactivated or attenuated isolate of *Equine* Influenza Virus (EIV). In some embodiments the compositions comprise at least one antigen of EIV. In some embodiments the EIV is selected from the group consisting of Clade 1 viruses, Clade 2 viruses, Influenza A/South Africa/2003, Influenza A/*equine*-2/Ohio/03, Influenza A/*equine*-2/New Market/2/93, Influenza A/*equine*-2/Kentucky/95, Influenza A/*equine*-2/Richmond/1/2007 and combinations thereof.

In one embodiment, along with the inactivated (or live, attenuated) one or more isolates of *Corynebacterium Pseudotuberculosis* Bacterin-Toxoid, the immunogenic compositions provided herein further comprise at least one antigen or one additional inactivated or live, attenuated isolate of *Equine* Influenza Virus and at least one antigen or one additional inactivated or live, attenuated isolate of *Equine* Herpes Virus. In some embodiments the compositions comprise at least one antigen of EHV and at least one antigen of EIV. In some embodiments the EHV is EHV-1 or EHV-4 or a combination thereof and the EIV is selected from the group consisting of Clade 1 viruses, Clade 2 viruses, Influenza A/South Africa/2003, Influenza A/*equine*-2/Ohio/03, Influenza A/*equine*-2/New Market/2/93, Influenza A/*equine*-2/Kentucky/95, Influenza A/*equine*-2/Richmond/1/2007 and combinations thereof.

In one embodiment, along with the inactivated (or live, attenuated) one or more isolates of *Corynebacterium Pseudotuberculosis* Bacterin-Toxoid, the immunogenic compositions provided herein further comprise at least one antigen or inactivated virus of one or more additional isolates selected from the group consisting of *Equine* Influenza Virus, *Equine* Herpes Virus, West Nile Virus, Eastern *Equine* Encephalomyelitis Virus, Western *Equine* Encephalomyelitis Virus, and Venezuelan *Equine* Encephalomyelitis Virus, and/or Tetanus Toxoid, and combinations thereof.

In one embodiment, along with the inactivated (or live, attenuated) one or more isolates of *Corynebacterium Pseudotuberculosis* Bacterin-Toxoid, the immunogenic compositions provided herein further comprise at least one additional inactivated or live, attenuated virus of a isolate selected from the group consisting of West Nile Virus, Eastern *Equine* Encephalomyelitis Virus, Western *Equine* Encephalomyelitis Virus, and Venezuelan *Equine* Encephalomyelitis Virus, and/or Tetanus Toxoid, and combinations thereof.

In one embodiment, provided is a method of making the immunogenic composition of the present invention. The method generally comprises the steps of combining an inactivated or live, attenuated *Corynebacterium Pseudotuberculosis* Bacterin-Toxoid and a pharmaceutically acceptable carrier.

In some embodiments the method further comprises the step of adding one or more additional *equine* virus antigens or inactivated or live, attenuated *equine* viruses. In another embodiment, the method further comprises the step of adding a suitable adjuvant to the composition.

In one embodiment, provided is a method for reducing the incidence of or lessening the severity of clinical symptoms associated with or caused by *Corynebacterium pseudotuberculosis* in an animal or a herd of animals comprising administering an immunogenic composition as disclosed herein to an animal in need thereof. In some embodiments, the animal is a horse.

The aforementioned embodiments may further contain one or more of the following features described below.

In some embodiments, the compositions also include inactivated or live, attenuated *Corynebacterium Pseudotuberculosis* Bacterin-Toxoid in combination with the following inactivated or live, attenuated viral isolates or antigens and combinations of isolates and antigens: West Nile Virus; Eastern *Equine Encephalomyelitis*; Western *Equine Encephalomyelitis*; Venezuelan *Equine Encephalomyelitis*; Tetanus Toxoid; Eastern *Equine Encephalomyelitis* and Western *Equine Encephalomyelitis*; Eastern *Equine*

Encephalomyelitis and Venezuelan Equine Encephalomyelitis; Eastern Equine Encephalomyelitis and Tetanus Toxoid; Eastern Equine Encephalomyelitis, Western Equine Encephalomyelitis, and Venezuelan Equine Encephalomyelitis; Eastern Equine Encephalomyelitis, Western Equine Encephalomyelitis, and Tetanus Toxoid; Eastern Equine Encephalomyelitis, Western Equine Encephalomyelitis, Venezuelan Equine Encephalomyelitis and Tetanus Toxoid; Western Equine Encephalomyelitis and Venezuelan Equine Encephalomyelitis; Western Equine Encephalomyelitis and Tetanus Toxoid; Western Equine Encephalomyelitis, Venezuelan Equine Encephalomyelitis, and Tetanus Toxoid; Venezuelan Equine Encephalomyelitis and Tetanus Toxoid; and Eastern Equine Encephalomyelitis, Venezuelan Equine Encephalomyelitis and Tetanus Toxoid, Equine Rhinitis Virus Type A (ERAV) Equine Rhinitis Virus Type B, as embodied in US Pub. No. US 2012-0237543 A1, hereby incorporated by reference, or antigens or antigenic components thereof. Further preferred embodiments of the present invention include immunogenic compositions made using each of the specified combination vaccines listed above and adding antigens or inactivated or attenuated viruses from Equine Herpesvirus, preferably type 1, type 4, (EHV1 and/or EHV4) or combinations thereof.

The immunogenic compositions as disclosed herein can be administered in any immunogenically effective dose. In a preferred embodiment, the immunogenic composition is administered as a single dose. Preferably, the dose has a total volume between about 0.5 mL and about 2.5 mL, more preferably between about 0.6 mL and about 2.0 mL, even more preferably between about 0.7 mL and about 1.75 mL, still more preferably between about 0.8 mL and about 1.5 mL, even more preferably between about 0.9 mL and about 1.25 mL, with a single dose about 1.0 mL being the most preferred.

In another embodiment, the immunogenic composition is administered with a first dose being administered prior to the administration of a second (booster) dose. Preferably, the second dose is administered at least about 15 days after the first dose. More preferably, the second dose is administered between about 15 and about 28 days after the first dose. Even more preferably, the second dose is administered at least about 17 days after the first dose. Still more preferably, the second dose is administered between about 17 and about 25 days after the first dose. Even more preferably, the second dose is administered at least about 19 days after the first dose. Still more preferably, the second dose is administered between about 19 and about 23 days after the first dose. Most preferably the second dose is administered at least about 21 days after the first dose. In a preferred embodiment, both the first and second doses of the immunogenic composition are in the same amount. Preferably, each dose is in the preferred amounts specified above, with a dose of about 1 mL for the first and second dose being most preferred. In addition to the first and second dose regimen, an alternate embodiment comprises further subsequent doses. For example, a third, fourth, or fifth dose could be administered in these embodiments. Preferably, subsequent third, fourth, and fifth dose regimens are administered in the same amount as the first dose, with the time frame between the doses being consistent with the timing between the first and second doses mentioned above, although the timing may also vary.

In one embodiment the immunogenic composition is administered in three doses. In some embodiments the three doses are administered at three week intervals.

In an embodiment that comprises Corynebacterium Pseudotuberculosis Bacterin-Toxoid, preferably CPS-002+1 05-13-13 (ATCC Accession No. PTA-121358), the amount of Corynebacterium Pseudotuberculosis Bacterin-Toxoid in the immunogenic composition is at least about $10^{2.0}$ CFU/dose. More preferably, the amount of Corynebacterium Pseudotuberculosis Bacterin-Toxoid is between about $10^{2.0}$ CFU/dose to about $10^{10.0}$ CFU/dose. Still more preferably, the amount of *Corynebacterium Pseudotuberculosis* Bacterin-Toxoid is at least about $10^{2.5}$ CFU/dose. Even more preferably, the amount of *Corynebacterium Pseudotuberculosis* Bacterin-Toxoid is between about $10^{2.5}$ CFU/dose to about $10^{9.5}$ CFU/dose. Still more preferably, the amount of *Corynebacterium Pseudotuberculosis* Bacterin-Toxoid is at least about $10^{3.0}$ CFU/dose. Even more preferably, the amount of *Corynebacterium Pseudotuberculosis* Bacterin-Toxoid is between about $10^{3.0}$ CFU/dose to about $10^{9.0}$ CFU/dose. Still more preferably, the amount of *Corynebacterium Pseudotuberculosis* Bacterin-Toxoid is at least about $10^{3.5}$ CFU/dose. Even more preferably, the amount of *Corynebacterium Pseudotuberculosis* Bacterin-Toxoid is between about $10^{3.5}$ CFU/dose to about $10^{9.0}$ CFU/dose. Sill more preferably, the amount of *Corynebacterium Pseudotuberculosis* Bacterin-Toxoid is between about $10^{6.5}$ CFUU/dose and about $10^{8.5}$ CFU/dose. More preferably, the amount of *Corynebacterium Pseudotuberculosis* Bacterin-Toxoid is between about $10^{7.0}$ CFU/dose and about $10^{9.0}$ CFU/dose. The CFU values of an inactivated or attenuated *Corynebacterium Pseudotuberculosis* Bacterin-Toxoid or any other inactivated or attenuated immunogenic composition or vaccine refer in general to the viral content in the final immunogenic composition or vaccine that however is equivalent to the viral content calculated for the vaccine composition prior to the inactivation of its virus. Preferably, the immunogenic composition of the present invention stimulates ELISA serum optical density antibodies to *Corynebacterium Pseudotuberculosis* Bacterin-Toxoid at an OD of at least 0.5, 1.0, 1.5, 2.0 or 2.5 at a serum dilution of 1:80.

In one embodiment, in each dose of an embodiment of the present invention that comprises one or more additional *equine* antigens, the amount of Eastern *Equine Encephalomyelitis* or Venezuelan *Equine Encephalomyelitis* in any dose is preferably at least about $10^{5.5}$ $TCID_{50}$/dose. Even more preferably, the dose is between about $10^{5.5}$ $TCID_{50}$/dose and about $10^{9.5}$ $TCID_{50}$/dose. Still more preferably, the dose is at least about $10^{6.0}$ $TCID_{50}$/dose. Still more preferably, the dose is between about $10^{6.0}$ $TCID_{50}$/dose and about $10^{9.0}$ $TCID_{50}$/dose. Even more preferably, the dose is at least about $10^{6.5}$ $TCID_{50}$/dose. Still more preferably, the dose is between about $10^{6.5}$ $TCID_{50}$/dose and about $10^{9.5}$ $TCID_{50}$/dose. Even more preferably, the dose is at least about $10^{7.0}$ $TCID_{50}$/dose. Most preferably, the dose is between about $10^{6.7}$ $TCID_{50}$ and about $10^{9.2}$ $TCID_{50}$/dose.

In an embodiment that comprises inactivated or killed WNV or antigen, the amount of WNV or antigen is at least about $10^{2.0}$ $TCID_{50}$/dose. More preferably, the WNV or antigen is between about $10^{2.0}$ $TCID_{50}$/dose to about $10^{10.0}$ $TCID_{50}$/dose. Still more preferably, the WNV or antigen is at least about $10^{2.5}$ $TCID_{50}$/dose. Even more preferably, the WNV or antigen is between about $10^{2.5}$ $TCID_{50}$/dose to about $10^{9.5}$$TCID_{50}$/dose. Still more preferably, the WNV or antigen is at least about $10^{3.0}$ $TCID_{50}$/dose. Even more preferably, the WNV or antigen is between about $10^{3.0}$ $TCID_{50}$/dose to about $10^{9.0}$ $TCID_{50}$/dose. Still more preferably, the WNV or antigen is at least about $10^{3.5}$ $TCID_{50}$/dose. Even more preferably, the WNV or antigen is between about $10^{3.5}$ $TCID_{50}$/dose to about $10^{9.0}$ $TCID_{50}$/dose. Most preferably, the WNV or antigen is between about $10^{7.0}$ TCID$_{50}$/dose and about $10^{9.0}$ TCID$_{50}$/dose. The TCID$_{50}$ values of an inactivated WNV vaccine or any other inactivated vaccine refer in general to the antigen content in the final vaccine that however is equivalent to the antigen content calculated for the vaccine composition prior to the inactivation of its antigen. Preferably, the immunogenic composition of the present invention stimulates serum neutralizing antibodies to WNV at a titer of at least 1:4 or higher. In some embodiments the titer is at least 1:5, 1:6, 1:7, 1:8, 1:9, 1:10, 1:11; 1:12, 1:13, 1:14, or 1:15 or higher. In some embodiments, the titer is no more than 1:300, 1:1050, 1:32000, 1:70000, or 1:140000. In a preferred embodiment, in each dose of an embodiment of the present invention that comprises additional equine antigen, the amount of Eastern Equine Encephalomyelitis or Venezuelan Equine Encephalomyelitis in any dose is preferably at least about $10^{5.5}$ TCID$_{50}$/dose. Even more preferably, the dose is between about $10^{5.5}$ TCID$_{50}$/dose and about $10^{9.5}$ TCID$_{50}$/dose. Still more preferably, the dose is at least about $10^{6.0}$ TCID$_{50}$/dose. Still more preferably, the dose is between about $10^{6.0}$ TCID$_{50}$/dose and about $10^{9.0}$ TCID$_{50}$/dose. Even more preferably, the dose is at least about $10^{6.5}$TCID$_{50}$/dose. Still more preferably, the dose is between about $10^{6.5}$ TCID$_{50}$/dose and about $10^{9.5}$ TCID$_{50}$/dose. Even more preferably, the dose is at least about $10^{7.0}$ TCID$_{50}$/dose. Most preferably, the dose is between about $10^{6.7}$ TCID$_{50}$ and about $10^{9.2}$ TCID$_{50}$/dose.

Preferably, the Western Equine Encephalomyelitis antigen, when present in the composition of the present invention, is in an amount of at least about $10^{6.2}$ TCID$_{50}$/dose. Even more preferably, the amount is between about $10^{6.2}$ TCID$_{50}$/dose and about $10^{10.2}$ TCID$_{50}$/dose. Still more preferably, the amount is at least about $10^{6.7}$ TCID50/dose. Even more preferably, the amount is between about $10^{6.5}$ TCID$_{50}$/dose and about $10^{9.7}$ TCID$_{50}$/dose. Still more preferably, the amount is at least about $10^{7.2}$ TCID$_{50}$/dose. Even more preferably, the amount is between about $10^{7.2}$ TCID$_{50}$/dose and about $10^{9.2}$ TCID$_{50}$/dose. Still more preferably, the amount is at least about $10^{7.7}$ TCID$_{50}$/dose with between about $10^{6.5}$ TCID$_{50}$/dose and about $10^{9.0}$ TCID$_{50}$/dose being the most preferred.

In another preferred embodiment, the amount of tetanus toxoid, if present in the composition of the present invention, is in an amount of at least about 3 CPU/dose, more preferably, between about 3 CPU and about 20 CPU, still more preferably, at least about 4 CPU, and most preferably, at least about 5 CPU but not more than about 50 CPU/dose.

In an alternate embodiment, where one or more isolates of Equine Influenza Virus is present, the amount of Equine Influenza present in the composition is in an amount of at least about $10^{5.0}$ TCID$_{50}$/dose. More preferably, the Equine Influenza is in an amount of between about $10^{5.0}$ TCID$_{50}$/dose to about $10^{9.0}$ TCID$_{50}$/mL, and, more preferably, at least about $10^{6.0}$ TCID$_{50}$/dose. Still more preferably, the amount is between about $10^{6.0}$ TCID$_{50}$/dose to about $10^{8.0}$ TCID$_{50}$/dose and, more preferably, the amount is at least about $10^{6.5}$ TCID$_{50}$/dose. Still more preferably, the amount is between about $10^{6.5}$ TCID$_{50}$/dose to about $10^{7.5}$ TCID$_{50}$/dose, with the most preferred amount being between about $10^{6.7}$ TCID$_{50}$/dose to about $10^{7.3}$ TCID$_{50}$/dose.

In an embodiment that comprises Equine Herpes Virus, the amount of Equine Herpes Virus in each dose is at least about $10^{6.0}$ TCID$_{50}$/dose. More preferably, Equine Herpes Virus is present in the composition in an amount of between about $10^{6.0}$ TCID$_{50}$/dose to about $10^{9.5}$ TCID$_{50}$/dose and, more preferably, in an amount of about $10^{7.0}$ TCID$_{50}$/dose. Still more preferably, Equine Herpes Virus is present in an amount between about $10^{7.5}$ TCID$_{50}$/dose to about $10^{9.0}$ TCID$_{50}$/dose and, more preferably, in an amount of about $10^{8.0}$ TCID$_{50}$/dose. Still more preferably, Equine Herpes Virus is present in an amount of between about $10^{8.0}$ TCID$_{50}$/dose to about $10^{9.0}$ TCID$_{50}$/dose and, most preferably, in an amount of about $10^{8.50}$ TCID$_{50}$/dose.

The present invention additionally provides for a method of reduction of the incidence of and/or severity of clinical signs associated with, Corynebacterium pseudotuberculosis infection in an animal, preferably a horse. Such methods generally comprise the step of administering a vaccine composition comprising an inactivated or live, attenuated isolate of Corynebacterium pseudotuberculosis and a pharmaceutically acceptable carrier. In some preferred embodiments, an adjuvant, particularly a carbomer such as HRA-5, is added to the composition, and in other preferred forms, no adjuvant is provided.

In an alternate preferred embodiment, the method comprises administering a vaccine composition comprising one or more inactivated or live, attenuated isolates of Corynebacterium Pseudotuberculosis Bacterin-Toxoid in combination with immunologically effective amounts of antigenic components or inactivated isolates from other equine pathogens. In some embodiments of the method, the pathogens in combination with the Corynebacterium pseudotuberculosis, are selected from the group consisting of antigens or inactivated or attenuated isolates of EHV and EIV and combinations thereof. In some embodiments the pathogens are antigens. In some embodiments the EHV is EHV-1 or EHV-4 or a combination thereof. In other embodiments the EIV is selected from the group consisting of Clade 1 viruses, Clade 2 viruses, Influenza A/South Africa/2003, Influenza A/equine-2/Ohio/03, Influenza A/equine-2/New Market/2/93, Influenza A/equine-2/Kentucky/95, Influenza A/equine-2/Richmond/1/2007 and combinations thereof.

In still other embodiments of the method, the pathogens in combination with the ERAV and/or ERBV isolates, are selected from the group consisting of antigens or inactivated or attenuated isolates of WNV, Eastern Equine Encephalomyelitis, Western Equine Encephalomyelitis, and Venezuelan Equine Encephalomyelitis, Equine Rhinitis Type A, Equine Rhinitis Type B, and tetanus toxoid, and combinations thereof, and more preferably being those combinations described above. In another preferred embodiment, the vaccine of the present invention is combined with a suitable adjuvant and/or pharmaceutically acceptable carrier.

Preferably, the ERAV isolate is ERAV/ON/05 (ATCC Accession No. PTA-11828) and the ERBV isolate is ATCC Accession NO: PTA-11829.

The present invention provides for reduction of the incidence of and/or severity of clinical symptoms associated with, Corynebacterium pseudotuberculosis infection in a herd. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to infection by Corynebacterium pseudotuberculosis. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms, or alternatively exhibit clinical symptoms of reduced severity. Advantageously, the present invention also provides protection from heterologous isolates (relative to the isolate used in the composition) of pathogens.

The present invention further provides a method of stimulating serum neutralizing or serum hemagglutination antibodies to a pathogen selected from the group consisting of ERAV, ERBV, WNV, WEE, VEE, EEE, EHV, EIV, and combinations thereof by administering a composition in accordance with the present invention described herein.

The immunogenic composition of the present invention provides an extended duration of immunity against all isolates present in the vaccine. Preferably, the duration of immunity against *Corynebacterium pseudotuberculosis* is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

The immunogenic composition of the present invention also provides an extended duration of immunity against all antigens present in the vaccine. Preferably, the duration of immunity against West Nile is at least 6 to 12 months, more preferably, the duration of immunity is at least 6 months, still more preferably, the duration of immunity is at least 12 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EIV is at least 6 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EHV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Western *Equine Encephalomyelitis* is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Eastern *Equine Encephalomyelitis* is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Venezuelan *Equine Encephalomyelitis* is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Tetanus Toxoid is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity of at least 12 months further relates to any combination of antigens forming the immunogenic composition of the present invention.

In one embodiment comprising an inactivated (or, alternatively live attenuated) ERAV and/or ERBV as disclosed herein, the immunogenic composition ameliorates shedding of infectious ERAV and/or ERBV to prevent spread of the virus to other susceptible animals. In some embodiments the compositions prevent shedding of the virus.

In one embodiment comprising EIV and/or EHV antigen, as described above, the immunogenic composition ameliorates shedding of infectious EIV or EHV to prevent spread of the virus to other susceptible animals.

In one embodiment, compositions in accordance with the present invention described herein overcome interference from passively acquired maternal immunity and stimulate active immunity and a reduction in the incidence of or severity of clinical signs of EIV infection in vaccinated animals against EIV.

In one embodiment of the present invention, an immunogenic composition comprising ERAV and/or ERBV, VEE, WEE, EEE, tetanus, WNV, *equine* rhinopneumonitis and *equine* influenza, all as described herein, demonstrates efficacy against ERAV, ERBV, VEE, WEE, EEE, tetanus, WNV, *equine* rhinopneumonitis and *equine* influenza after administration in accordance with the present invention. Preferably, such a composition will further include an adjuvant, preferably a carbomer such as HRA-5, and/or mineral oil, and a pharmaceutically acceptable carrier. In preferred forms, the composition will be administered in a single, 1 mL dose. In some embodiments composition is administered in two doses or preferably three doses, with each dose separated by 1, 2, 3, and 4 weeks.

Each of the immunogenic compositions described herein that include ERAV, particularly ERAV/ON/05 (ATCC Accessions NO: PTA-11828) and other isolates as described supra, and/or ERBV, particularly a ERBV isolate having ATCC Accession NO: PTA-11829, or others as also described supra, can be administered as described such that they reduce the incidence of or lessen the severity of clinical symptoms associated with ERAV and/or ERBV, such as pyrexia, elevations in temperature, increased lung sounds, lymphadenopathy, nasal discharge, ocular discharge, pharyngitis, edema of legs, cough, and in the case of ERAV, increased incidence of abortion in pregnant mares. In some aspects, the compositions lessen the amount or length of nasal or ocular discharge or the length of time that such symptoms are presented. In some aspects, animals inoculated with the compositions show no clinical symptoms of ERAV and/or ERBV infection one week or longer after exposure to ERAV and/or ERBV. In other aspects, animals inoculated with the compositions show no clinical symptoms of ERAV and/or ERBV infection when exposed to ERAV and/or ERBV. Clinical symptoms of ERAV and ERBV may be scored such as according to Table 3 in Example 2, Table 14 in Example 4, or Table 17 in Example 5.

Each of the immunogenic compositions described herein that include EIV antigen or inactivated EIV and can be administered as described such that they reduce the incidence of or lessen the severity of clinical symptoms associated with *Equine* Influenza Virus.

The present invention also provides a method for reducing the incidence of or lessening the severity of clinical symptoms associated with *Equine* Herpes Virus comprising the step of administering any one of the immunogenic compositions described above containing EHV antigen or inactivated or attenuated EHV to an animal.

The present invention also provides a method for reducing the incidence of clinical symptoms associated with West Nile Virus comprising the step of administering any one of the immunogenic compositions that includes WNV antigen or inactivated or attenuated WNV, as described herein, to an animal.

The present invention also provides a method for reducing the incidence of clinical symptoms associated with *Equine* Influenza Virus comprising the step of administering any one of the immunogenic compositions described above, that includes an EIV antigen or inactivated or attenuated EIV, to an animal.

The present invention further provides a method for reducing the incidence of clinical symptoms associated with *Equine* Herpes Virus comprising the step of administering any one of the immunogenic compositions described above that includes an EHV antigen or inactivated or attenuated EHV, to an animal.

The present invention provides a method of reducing the incidence of bacterial infection in a herd comprising the step of administering any one of the immunogenic compositions described above to an animal, wherein the reduction of incidence of infection, compared to herds not receiving the immunogenic composition, is from about 10% to about 50% reduction. In one embodiment the compositions provided herein reduce ERAV infection by 10% to 50%. In other embodiments the compositions provided herein reduce ERBV infection by 10% to 50%.

The present invention provides a method for reducing the incidence of or lessening the severity of clinical symptoms associated with *Equine* Herpes Virus comprising the step of administering any one of the immunogenic compositions disclosed herein, that includes an EHV antigen or inactivated or attenuated EHV, to an animal.

The present invention provides a method for reducing the incidence of or lessening the severity of clinical symptoms associated with *Equine* Influenza Virus in a herd, comprising the step of administering any one of the immunogenic compositions disclosed herein, that includes an EIV antigen or inactivated or attenuated EIV, to an animal.

The present invention provides a method for reducing the incidence of or lessening the severity of clinical symptoms associated with West Nile Virus in a herd, comprising the step of administering any one of the immunogenic compositions disclosed herein, that includes a WNV antigen or inactivated or attenuated WNV, to an animal.

The present invention provides a method for reducing the incidence of or lessening the severity of clinical symptoms associated with Eastern *Equine Encephalomyelitis* in a herd, comprising the step of administering any one of the immunogenic compositions disclosed herein that includes an EEE virus antigen or an inactivated or attenuated EEE virus, to an animal.

The present invention further provides a method for reducing the incidence of or lessening the severity of clinical symptoms associated with Western *Equine Encephalomyelitis* in a herd, comprising the step of administering any one of the immunogenic compositions disclosed herein, that includes a WEE virus antigen or an inactivated or attenuated WEE virus, to an animal.

The present invention further provides a method for reducing the incidence of or lessening the severity of clinical symptoms associated with Venezuelan *Equine Encephalomyelitis* in a herd, comprising the step of administering any one of the immunogenic compositions disclosed herein, that includes a VEE virus antigen or an inactivated attenuated VEE virus, to an animal.

The aforementioned embodiments may be used in a combination therapy or as part of an immunization schedule in combination with other immunogenic agents and vaccines. In one embodiment, the compositions provided herein are used in combination with the immunogenic agents and vaccines described in WO 2010/025469, which is incorporated herein by reference in its entirety.

The present invention also provides a method of making any one of the immunogenic composition as described above and herein, comprising the steps of combining an inactivated or live, attenuated ERAV or ERBV with a suitable pharmaceutical carrier. In preferred forms, this method further comprises the step of adding one or more *equine* antigens or inactivated or attenuated viruses. A preferred group of *equine* antigens and viruses are selected from the group consisting of West Nile Virus, Western *Equine Encephalomyelitis*, Eastern *Equine Encephalomyelitis*, Venezuelan *Equine Encephalomyelitis*, EHV, and EIV, and tetanus toxoid, and combinations thereof. In some preferred forms, the methods described herein can further comprise a filtration step, wherein the final product is in a more pure form.

"About" refers to ±10% of the specified quantity.

"Animals" as used herein includes domesticated animals including dogs and hooved animals including equidae, and specifically, horses. In some embodiments, the term also refers to a human.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion, HRA-3 (acrylic acid saccharide cross-linked polymer), HRA-3 with cottonseed oil (CSO), or preferably an acrylic acid polyol cross-linked polymer. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® brand products, especially L121. See Hunter et al., The Theory and Practical Application of Adjuvants (Ed. Stewart-Tull, D. E. S.) John Wiley and Sons, NY, pp 51-94 (1995) and Todd et al., Vaccine 15:564-570 (1997). In a preferred embodiment the adjuvant is at a concentration of about 0.01 to about 50%, preferably at a concentration of about 2% to 30%, more preferably at a concentration of about 5% to about 25%, still more preferably at a concentration of about 7% to about 22%, and most preferably at a concentration of about 10% to about 20% by volume of the final product.

As used herein, "a pharmaceutically acceptable carrier" or "pharmaceutical carrier" includes any and all excipients, solvents, growth media, dispersion media, coatings, adjuvants, stabilizing agents, diluents, preservatives, inactivating agents, antimicrobial, antibacterial and antifungal agents, isotonic agents, adsorption delaying agents, and the like. Such ingredients include those that are safe and appropriate for use in veterinary applications. In some preferred embodiments, and especially those that include lyophilized immunogenic compositions, stabilizing agents for use in the present invention include stabilizers for lyophilization or freeze-drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In a preferred embodiment, the immunogenic composition of the present invention is prepared comprising a preservative and a stabilizer; and, more preferably, the immunogenic composition of the present invention is prepared comprising Amphotericin, formaldehyde, gentamycin, EDTA, glycerol, and combinations thereof.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

The term "in need of such administration" or "in need of such administration treatment," as used herein means that the administration/treatment is associated with the boosting or improvement in health or any other positive medicinal effect on health of the animals which receive the immunogenic composition in accordance with the present invention, such as reducing the incidence or severity of a viral infection or disease.

"*Equine* rhinitis A virus (ERAV)" refers to an Aphthovirus in the family Picornaviridae, and was previously known as *Equine* rhinitis 1. "ERAV" as used herein includes inactivated forms. In one embodiment, the ERAV is isolate ERAV/ON/05 having accession number PTA-11829 deposited on Apr. 14, 2011 with the ATCC (American Type Culture Collection, P.O. Box 1549 Manassas, Va. 20108 USA) in accordance with the Budapest Treaty, and that was recovered from Rabbit-kidney-13 (RK-13) cell culture from a nasal swab from a horse in Ontario Canada in 2005. The ERAV/ON/05 when reverse transcribed and sequenced has SEQ ID NO: 1 in its 5' UTR region.

"*Equine* rhinitis B virus (ERBV)" refers to an Erbovirus in the family Picornaviridae, and was previously known as *Equine* rhinitis 2. "ERBV" as used herein includes inactivated forms. In one embodiment, the ERBV is a isolate deposited with the ATCC that was recovered from Rabbit-kidney-13 (RK-13) cell culture from a nasal swab from a horse in Ontario Canada (ATCC Accession NO: PTA-11828) that was deposited with the ATCC (American Type Culture Collection, P.O. Box 1549 Manassas, Va. 20108 USA) on Apr. 14, 2011 under the Budapest Treaty. The ERBV isolates useful in the immunogenic compositions of the invention have genomic sequences that when reverse transcribed into DNA are greater than 85%, 90%, 95%, 98%, 99% or 100% identical to the reverse transcript of the genomic sequence of the ERBV isolate having ATCC Accession No. PTA-11829, or have polyprotein coding sequences that are more than 97%, 98%, 99%, or 100% identical to the polyprotein coding sequence of the ERBV isolate having ATCC Accession No. PTA-11829. In some embodiments, the ERBV isolates useful in the invention have polyproteins with an amino acid sequence greater than 95%, 95%, 97%, 98%, 99%, or 100% identical to the polyprotein sequence of the ERBV isolate having ATCC Accession No. PTA-11829. In yet other embodiments, the ERBV has an L protein, VP4, VP2, VP3, VP1, 2A, 2B, 2C, 3A (Vpg), 3B, 3Cpro, 3Dpol that have an amino acid sequence with greater than 80%, greater than 90%, greater than 99%, or 100% identity to the same protein found in the ERBV isolate having ATCC Accession No. PTA-11829. All of the ERBV isolates are, when not inactivated or attenuated, infective and able to replicate in host cells.

The term "West Nile Virus" antigen means, but is not limited to the components of the WNV virion that are immunogenic when present in an animal, and most particularly protein components, such as envelope and non-structural proteins, of the WNV that provoke humoral or cellular immune responses when present in an animal. Such antigens can include DNA, protein subunits, modified live virus, and inactivated virus. In preferred forms of the invention, the WNV antigen or antigens comprise inactivated or killed, and even more preferably, North American dominant, WNV isolates.

The term "North American West Nile Virus (isolates)" refers to, but is not limited to any West Nile Virus isolate that has ever been discovered on the North American continent. Preferably, a North American West Nile Virus isolate has a sequence identity to the NY99 isolate (GenBank accession no. AF196835 or NCBI reference sequence NC_00942.1 of at least 97%, even more preferably, at least 98%, still more preferably, at least 98.5%, more preferably, at least 99%, even more preferably, at least 99.2%, and, most preferably of at least 99.4%. WN02 is a representative example of a WNV isolate that can be referred to as a North American Dominant West Nile Virus isolate. Specifically, North American Dominant isolates are those having at least 1 nucleotide change resulting in an amino acid change from the WN99 isolates. Isolate NY99 (GenBank accession no. AF196835) serves as a reference isolate for determining if an isolate is North American Dominant. In addition, these isolates may have one or more silent amino acid changes. In some embodiments, the nucleotide change results in an amino acid change in an envelope protein of the isolate and, more preferably, the nucleotide change results in an amino acid change from valine to alanine. Preferably, this amino acid change is associated with a greater ability to replicate in the intermediate host, namely, the mosquito. More preferably, North American Dominant isolates include either (and preferably both) a U to C mutation and a C to U mutation at positions 1442 and 2466 (in comparison to a North American isolate, e.g., NY 99), respectively. Still more preferably, North American Dominant isolates further include a mutation in the nucleotide sequence encoding the E protein and the C to U mutation at position 9352 in the sequence encoding the NS5 protein (again in comparison to a North American isolate, e.g., NY 99). These preferred mutations are shown in Phylogenetic Analysis of North American West Nile Virus Isolates, 2001-2004: Evidence for the Emergence of a Dominant Genotype, C. Todd Davis, et al., Virology 342, p. 252-265 (2005), the teaching and content of which is hereby incorporated by reference. West Nile Virus isolates, for purposes of the present invention, are not limited to horse and *equine* West Nile Virus isolates but encompass, while not being limited to, those West Nile Virus isolates of bird origin, donkey origin, pig origin, human origin, mammal origin, and *equine* origin.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity. In the present disclosure, it is understood that SEQ ID NO:1 (5' UTR) and SEQ ID NO:2 are the DNA sequences that result from reverse transcription of the 5' UTR and the entire genome of ERAV/ON/05, respectively. Likewise, SEQ ID NO:3 refers to the amino acid sequence corresponding to the polyprotein encoded by the genomic sequence of ERAV/ON/05. Percent identity of a given ERAV isolate in comparison to SEQ ID NO:1 or SEQ ID NO:2 is thus meant to refer to the corresponding DNA sequence resulting from reverse transcription and sequencing.

"CFU" refers to colony forming units of the bacterium on a growth media.

For purposes of the present invention the terms "isolate" and "isolate" have the same meaning and are used interchangeably.

"Clinical signs" or "clinical symptoms" for *Corynebacterium pseudotuberculosis* include but are not limited to external abscesses, deep intramuscular and internal abscesses, elevation in temperature, edema of the legs, loss of weight and lameness.

"Clinical signs" or "clinical symptoms" of ERAV or ERBV, for purposes of this invention, include, but are not limited to pyrexia, elevation in temperature, increased lung sounds, lymphadenopathy, nasal discharge, ocular discharge, and cough, and pharyngitis. Still other signs or symptoms include anemia, anorexia, lymphadenitis of the head and neck, edema of the legs, lethargy, and pain. Additionally, clinical signs of ERAV and/or ERBV infections may include those associated with *Equine* Herpes virus and *Equine* Influenza virus. In one embodiment the clinical signs for ERAV include cough, pharyngitis, pyrexia, elevations in temperature, increased submandibular lymph node size, nasal discharge, and ocular discharge. In certain embodiments, the clinical signs of ERAV include an increased incidence of abortion in pregnant mares. In another embodiment the clinical signs to be addressed by an immunological composition disclosed herein are those of respiratory infections, such as those caused by one or more of ERAV, ERBV, EIV, EHV-1, and EHV-4.

"Clinical signs" or "clinical symptoms" of West Nile Virus, for purposes of this invention, include, but are not limited to, symptoms or lesions associated with encephalitis, viremia, anorexia, depression, fever, weakness, abnormal gait, paralysis of hind limbs, impaired vision, ataxia, aimless wandering, convulsions, inability to swallow, coma, posterior weakness, paralysis, poor coordination, depression and related behavior, tremors, convulsions, paddling of the limbs, neurological problems, swelling of the central nervous system, death, and combinations thereof. The clinical signs exhibited by an infected animal vary depending on the severity of infection.

"Clinical Signs" or "clinical symptoms" of *Equine* Herpes virus, for purposes of this invention include, but are not limited to, abortion, neurological deficiencies, respiratory disease, reproductive system deficiencies and failure, and symptoms relating to the central nervous system. Additionally, clinical symptoms of EHV1 include, but are not limited to, the phenomenon of foals infected with EHV1, exhibiting respiratory complications, passing the virus to the older members of the herd who then exhibit reproductive deficiencies, including abortion, and neurological deficiencies, normally exhibited in the central nervous system.

"Clinical Signs" or "clinical symptoms" of Eastern *Equine Encephalomyelitis*, Western *Equine Encephalomyelitis*, and Venezuelan *Equine Encephalomyelitis*, for purposes of the present invention are those symptoms normally known to be associated with *encephalomyelitis*, including, but are not limited to fever, nervous signs such as sensitivity to sound, periods of excitement, and restlessness, brain lesions, drowsiness, drooping ears, circling, abnormal gait, paralysis, loss of appetite, depression, head pressing, lack of coordination, long-term disability, brain damage, death, and combinations thereof. "Safety" as used herein, refers to the absence of adverse consequences in the vaccinated animal following vaccination, including but not limited to, potential reversion of vaccine virus to virulence and clinically significant side effects, such as persistent systemic illness or unacceptable inflammation at the site of vaccine administration.

"Reduction of the incidence and/or severity of clinical signs" or "reduction in the incidence and/or severity of clinical symptoms," as referred to herein, means reducing the number of infected animals in a group, reducing or eliminating the number of animals exhibiting clinical signs of infection, or reducing the severity of any clinical signs that are present in the animals, in comparison to wild-type infection. For example, such clinical signs included but not limited to external abscesses, intramuscular abscesses, internal abscesses lameness, loss of weight, edema of the legs, and elevation of body temperature. Preferably, these are reduced in animals receiving the composition of the present invention by at least 10% in comparison to animals not receiving the vaccination which may become infected. More preferably, clinical signs are reduced in animals receiving the composition of the present invention by at least 20%, more preferably by at least 30%, even more preferably by at least 40%, and even more preferably by at least 50%.

"Duration of Immunity," as used herein, refers to the minimum number of days during which an animal produces an immunogenic response such that the animal will be relatively immune from contracting a bacteria or virus and/or benefit from reduction of incidence and/or severity of clinical signs, as described herein.

The term "inactivated" and "inactivated virus" refers to a previously virulent virus that has been irradiated (UV, X-ray or gamma radiation), heated or chemically treated to inactivate, kill, or otherwise modify the virus to substantially eliminate its virulent properties while retaining its immunogenicity. In a preferred embodiment, the inactivated viruses disclosed herein are inactivated by treatment with an inactivating agent. Suitable inactivating agents include betapropiolactone, binary or beta-ethyleneimine (BEI), glutaraldenyde, ozone, and Formalin (formaldehyde). In some embodiments, the inactivating agent is formaldehyde.

The terms "vaccine" and "immunogenic composition", when used herein, are meant to be used interchangeably.

Any West Nile Virus isolate(s) or isolate(s) can be used in accordance with the present invention. In a preferred embodiment, the isolate is selected from one or more of the following: New York (Northeastern North American) Isolate (WN-NY 99), Horse Origin, 1999, New York (Northeastern North American) Isolate (WN-NY 99), Crow Origin, 1999, United States Department of Agriculture Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof, and in a more preferred embodiment the isolate is selected from one or more of the following: United States Department of Agriculture Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof. In a most preferred embodiment, the isolate is United States Department of Agriculture Isolate 405330 (USDA 2005), Horse Origin singularly or in combination with one or more isolates as listed above. In an additionally preferred embodiment, those isolates which are part of the North American West Nile Virus isolates are included. In yet another preferred embodiment North American Dominant West Nile Virus isolates are included. In addition to those listed above, specific isolates include, but are not limited to, WN02 and isolates which have at least 1, preferably at least 2, and even more preferably at least 3 nucleotide changes resulting in at least one amino acid change from the WN NY99 isolates, and most preferred are isolates with the amino acid change from valine to alanine at position 159 of the envelope protein. Most preferred North American Dominant isolates include, but are not limited to: NY2002Nassau, NY2002Clinton, NY2002Queens, GA20021, GA20022, TX20021, TX20022, IN2002, NY2003Albany, NY2003Suffolk, NY2003Chatauqua, CO20031, CO20032, TX2003, TX2003Harris4, TX2003Harris6, TX2003Harris7, TX2003Harris10, AZ2004, and TX2004Harris4, and combinations thereof. The isolates of West Nile Virus useful in the vaccine or immunogenic composition of the present invention can be any isolate or isolate. In a preferred embodiment, the North American Dominant West Nile Virus isolate used is either E-159 (Horse Origin) or E-159 (Donkey Origin). A representative isolate of such a North American Dominant WNV isolate includes the Horse Origin 2005 isolate deposited with the ATCC (ATCC Accession NO: PTA-9409), located at 10801 University Boulevard, Manassas, Va., 20110-2209, on Aug. 14, 2008, under the provisions of the Budapest Treaty. Equine Influenza isolates useful in the vaccine or immunogenic composition of the present invention can be any isolate or isolate. Representative isolates include Equi-2/Ohio/03, deposited as ATCC Accession NO: PTA-9522, Equi-2/Kentucky/95, deposited as ATCC Accession NO: PTA-9523, and Equi-2/New Market/2/93, deposited as ATCC Accession NO: PTA-9524. Representative isolates ATCC Accession Nos. PTA-9522, PTA-9523, and PTA-9524 were each deposited with the ATCC at 10801 University Boulevard, Manassas, Va., 20110-2209 on Sep. 23, 2008, under the provisions of the Budapest Treaty.

*Equine* Herpes Virus ("EHV") isolates useful in the vaccine or immunogenic composition of the present invention can be any isolate or isolate. Representative isolates include EHV Subtype 1, deposited as ATCC Accession NO: PTA-9525, and EHV Subtype 4, deposited as ATCC Accession NO: PTA-9526. Representative isolates ATCC Accession Nos. PTA-9525 and PTA-9526 were each deposited with the ATCC at 10801 University Boulevard, Manassas, Va., 20110-2209 on Sep. 23, 2008, under the provisions of the Budapest Treaty.

Western *Equine Encephalomyelitis* isolates useful in the vaccine or immunogenic composition of the present invention can be any isolate or isolate. A representative isolate includes the Fleming Isolate, deposited with the ATCC (ATCC Accession NO: PTA-9410), located at 10801 University Boulevard, Manassas, Va., 20110-2209, on Aug. 14, 2008, under the provisions of the Budapest Treaty.

Venezuelan *Equine Encephalomyelitis* isolates useful in the vaccine or immunogenic composition of the present invention can be any isolate or isolate. A representative isolate includes the TC-83 isolate, deposited with the ATCC (ATCC Accession NO: PTA-9411), located at 10801 University Boulevard, Manassas, Va., 20110-2209, on Aug. 14, 2008, under the provisions of the Budapest Treaty.

Eastern *Equine Encephalomyelitis* isolates useful in the vaccine or immunogenic composition of the present invention can be any isolate or isolate. A representative isolate includes the NJO isolate, deposited with the ATCC (ATCC Accession NO: PTA-9412), located at 10801 University Boulevard, Manassas, Va., 20110-2209, on Aug. 14, 2008, under the provisions of the Budapest Treaty.

Tetanus toxoid isolates useful in the vaccine or immunogenic composition of the present invention can be any isolate or isolate. A representative isolate is that taken from a master seed of *Clostridium tetani* from The Massachusetts Department of Public Health Institute of Laboratories in Boston, Mass.

The vaccine or immunogenic composition as disclosed herein is safe for administration in *Corynebacterium pseudotuberculosis*-susceptible species, including but not limited to ovine, caprine or hircine, and *equine* particularly *equine*, at any age. In a preferred embodiment, the present invention is safe for administration to foals 12 months of age or older, more preferably, it is safe for administration to foals 10 months of age or older, more preferably, it is safe for administration to foals 8 months or older, more preferably, it is safe for administration to foals 6 months of age or older, more preferably, is safe for administration to foals 4 months of age or older, more preferably, it is safe for administration to foals 2 months of age or older, more preferably, it is safe for administration to foals 1 month of age or older, even more preferably, it is safe for administration to foals between 1 day and 1 month of age, and, most preferably, it is safe for administration to foals 1 day of age or older.

The compositions as disclosed herein can be administered in any conventional manner. Examples of administration methods include any that afford access by cells of the immune system to the immunogenic composition including oral, transdermal/intradermal, intravenous, subcutaneous, intramuscular, intraocular, intraperitoneal, intrarectal, intravaginal, intranasal, intragastrical, intratracheal, intrapulmonarial, or any combination thereof. In a preferred embodiment, the vaccine is administered parenterally, preferably intranasally, subcutaneously, or intramuscularly, and in the most preferred embodiment the vaccine is administered intramuscularly.

In one embodiment, provided is a method for preparing and immunogenic composition comprising *Corynebacterium pseudotuberculosis* as disclosed herein. In one embodiment, the method comprises:

a) growing the virulent *Corynebacterium pseudotuberculosis* organism in growth media which allows high CFU/mL titer and high Phospholipase D production by the organism Toxoid;
b) harvesting the bacteria, phospholipase D and media;
c) contacting the bacteria, phospholipase D, and media with an inactivating agent to obtain the inactivated *Corynebacterium Pseudotuberculosis* Bacterin-Toxoid, and;
d) filtering the media to yield a purified *Corynebacterium Pseudotuberculosis* organism and phospholipase D toxoid. In one embodiment, the method comprises providing *Corynebacterium pseudotuberculosis* isolate having ATCC Accession NO: PTA-121358. Suitable growth media include Tryptic Soy Broth).

In one embodiment and in accordance with the methods disclosed herein, provided is an immunogenic composition comprising *Corynebacterium pseudotuberculosis* isolate having ATCC Accession NO: PTA-121358 and Amphotericin B, gentamicin sulfate, formaldehyde, and an adjuvant prepared according to the methods disclosed herein.

EXAMPLES

The following examples are set forth below to illustrate specific embodiments of the present invention. These examples are merely illustrative and are understood not to limit the scope or the underlying principles of the present invention.

Example 1

This example illustrates one embodiment of a *Corynebacterium pseudotuberculosis* composition in accordance with the present invention.
Materials and Methods
The original strain of *Corynebacterium pseudotuberculosis* (*C. pseudotuberculosis*) as isolate number SM 89. The bacteria was passed once onto blood agar and then once into TSB for the pre-master bacteria. The 12 mL of pre-master bacteria was used to inoculate a 2 L amount of TSB to make the Master Bacteria. The Master Bacteria was designated as *C. pseudotuberculosis* Lot 061512. The Master Bacteria was stabilized with 50% glycerol and put into 4 mL tubes and frozen at −80° C.

The master seed, working seed, and production cultures were tested using a gram stain when each seed or culture was established. Purity of the culture was determined by Gram's stain of subculture made using media described in 9 CFR 113.26(a).
Composition
Tryptic Soy Broth (TSB), Becton-Dickenson #211822 or equivalent, Purified Water, Sodium Hydroxide (NaOHa) or Hydrochloric Acid (HCl) for pH adjustment
Formulation
80-90% of the final volume of purified water was added to an appropriate mixing vessel. While mixing, TSB powder is added to the purified water. A hot stir plate may be used to aid in dissolving the powder. After mixing water is added to bring the volume up to the final described level. Mix for about 15 minutes, and adjust the pH to 7.3±0.2 using Sodium Hydroxide or Hydrochloric Acid if needed. Cover the mixing vessel after the pH is adjusted, if needed, and mix for 30 minutes. Dispense the media, if needed, and sterilize (121 degrees C.) for a minimum of 35 minutes. After sterilization is complete, the media was allowed to cool to room temperature under a hood.
Method of Preparing Suspensions for Seeding or Inoculation
Working seed is prepared from Master Seed Bacteria. For example, the entire content of a vial of MSB was used to inoculate 100 to 500 mL of seed medium. The culture was incubated at 36-39° C. for 12-24 hours. The culture was dispensed, stabilized with 10 to 50% glycerol, and stored at −70° C. or lower. Production cultures are prepared by inoculating an appropriate volume of seed medium with 1-10% total container volume with master seed or working seed and incubating at 36-39° C. for 12-24 hours. The volume of seed medium inoculated is dependent on the size of the production run. Production seed cultures are examined for purity using Gram's stain method at the time of harvest.
Time and Conditions for Incubation
Seed and Production cultures are incubated at 36-39° C. under anaerobic conditions for 12-24 hours under constant mixing (100-300 rpm). The pH is monitored during the growth phase and adjusted to maintain a pH of 7.0±0.2.
Character and Amount of Growth; Observation as to Contamination of Growth
Seed and Production cultures are examined for purity prior to harvest by Gram's stain. Cultures will be monitored by pulling a sample and checking the optical density (600 nm) during the growth phase. Cultures will be harvested when a minimum of 0.6 O.D. at 600 nm is achieved.
Incubation Period to Time of Harvest
Seed and Production cultures are incubated at 36-39° C. for 12-24 hours and until the Optical Density at 600 nm is a minimum of 0.6
Technique of Harvesting Micro-organisms for Production Purposes
Bacterin fluids are harvested when the optical density at 600 nm reaches a minimum of 0.6. Harvest material is pooled or held in the production vessels up to three days at 2-8° C. prior to inactivation.
Method of Inactivation
The cultures are inactivated by the addition of formalin, 0.50% and incubated at 35-39° C. for at least 72 hours. Gentamicin sulfate at 30 µg/mL and Amphotericin B at 2.0-2.5 µg/mL were added to the composition and a carbomer adjuvant, HRA Proprietary Adjuvant 5 (MVP Laboratories, Omaha, Nebr., Establishment License No. 301) was added to a final concentration of 10% by volume in the final product. Amphotericin B was added at a final concentration of 2.0-2.5 µg/mL. Adjuvant was added during serial formulation (10% v/v).

Inactivated bacterin fluids are concentrated by a factor of 5× to 20× using tangential flow ultrafiltration membrane cartridges with a molecular weight cut-off rating of 10,000 Dalton MW. The final concentrate is washed with a PBS solution.

Concentrated lots or fluids were combined to provide a calculated titer of at least 106.7 CFU/mL in the final product. Various lots may be blended to achieve the titer requirements per dose. In addition, the phospholipase D toxoid content in the culture media after the PBS wash was measured by spectrophotometric methods. The minimum phospholipase D toxoid content will be determined based on the efficacy serial.

The vaccine is given by typical hypodermic injection, with booster vaccinations if desired.

Example 2

This investigation was carried out to obtain an efficacy evaluation of a *Corynebacterium Pseudotuberculosis* Bacterin-Toxoid immunogenic composition to protect horses from challenge with *Corynebacterium pseudotuberculosis*.

Horses were selected by random number generator to be challenged with a virulent live strain of *Corynebacterium pseudotuberculosis*. Ten control horses and ten IVP-vaccinated horses were selected and moved to the indoor research facility. Horses were commingled throughout the challenge period in an enclosed 25,000 sq. ft. barn that was equipped with mosquito netting and insecticide foggers. All doors, passageways and air handling systems throughout the barn were carefully sealed with caulking and insulation to limit any possibility of entry of flies into the facility. All equipment, hay and wood shavings were staged within an enclosed area and fogged with intermittent insecticide spray for 24 hours prior to entering the horse area for feeding, cleaning or removing waste, in order to keep flies within the facility to a minimum.

On Day 48 post-2nd vaccination and Day 49 post-2nd vaccination, each horse was inoculated intradermally with 0.25 mL (containing 5,000 CFU) of *C. pseudotuberculosis* isolate 228. The inoculations were given in the midline pectoral region of the chest of each horse on each day. Prior challenge model development activities using this isolate found that intradermal inoculation of bacteria resulted in a disease syndrome that mimicked natural infection in horses.

Observations of horses included temperature evaluation on the Day of Challenge and for 3 days post-challenge, then every other day temperature evaluation until 12 days post-challenge. No elevated temperatures were found on any day of evaluation. Blood for serum evaluation was collected on the Day of Challenge and at 7, 14, 21, 28, 36 and 42 days post-challenge. The results are graphically illustrated in FIGS. 1-6.

Lesion size was measured daily using calibrated calipers and was recorded for height, width and depth of lesion in millimeters. A volume measurement was determined for each horse on each day and is listed and depicted below in the figures for each animal. Several horses were removed from the study due to the large size of their abscesses, and were treated with EXCEDE® (ceftiofur, Zoetis) after being measured on that day. Each horse was measured until it was evident that total resolution of lesions from several remaining horses would be improbable without antibiotic treatment.

Example 3

This example illustrates the evaluation of antibody response to a *Corynebacterium Pseudotuberculosis* Bacterin-Toxoid vaccine. Sera used in this study were those from horses given a 2-dose vaccination regimen of a monovalent *Corynebacterium Pseudotuberculosis* Bacterin-Toxoid vaccine. Blood was evaluated weekly for 3 weeks for antibody response to vaccination.

Serological responsiveness to an inactivated monovalent *Corynebacterium Pseudotuberculosis* Bacterin-Toxoid vaccine was evaluated in horses. Twenty (20) horses were vaccinated intramuscularly with two doses of a 1 mL vaccine at an antigen inclusion level of $10^{6.7}$ CFU/mL administered in a 21 day interval between doses. Twenty (20) additional horses received two, 1 mL intramuscular injections of adjuvanted media as placebo (Lot 052413-NEG) in a 21 day interval between doses. Sera from all study horses collected on Day 0 (day of first vaccination), Day 7, Day 21 (Day of Booster Vaccination), Day 28, Day 35 and Day 42 (end of study) were evaluated using a direct bind ELISA assay designed to detect an IgG isotype antibody response. Serological data in this report indicate that this vaccine significantly stimulates antibody to *Corynebacterium pseudotuberculosis* antigen which has been shown to be protective in other species (See, Evaluation of a commercially available vaccine against *Corynebacterium pseudotuberculosis* for use in sheep. Piontkowski, M. D.; Shivvers, D. W. Journal of the American Veterinary Medical Association 1998 Vol. 212 No. 11 pp. 1765-1768, hereby incorporated by reference).

The vaccine used in this study was a monovalent, inactivated *Corynebacterium Pseudotuberculosis* Bacterin-Toxoid. This vaccine is intended to reduce the clinical signs of *Corynebacterium pseudotuberculosis* infection.

Objective

The objective of this study was to evaluate antibody response to a *Corynebacterium Pseudotuberculosis* Bacterin-Toxoid experimental vaccine. Serum used in this study was that from horses given a 2-dose vaccination regimen with a 21-day interval between doses.

Material and Methods

*Corynebacterium pseudotuberculosis* Master Seed Bacteria is lot 061512. The approval date of the Master Seed Bacteria is Jan. 9, 2013.

Vaccine lot 052413 was produced in the manufacturing facility of Hennessy Research Associates, LLC, Est. Lic. 597 in accordance with the Outline of Production for Product Code 7A94.01.

The final formulated vaccine contained the following ingredients per 1 mL dose:
  *Corynebacterium pseudotuberculosis* $10^{6.7}$ CFU/mL
  Adjuvant (MVP Laboratories, S.O. #25) 100 µL
  Glycerol 100 µL
  Diluent, PBS containing q.s.
  Gentamicin, 30 µg/mL of diluent volume
  Formaldehyde, 0.1% of diluent volume
  Amphotericin B, 2.5 µg/mL
  Placebo lot 052413-neg The final formulated placebo vaccine contained all components of vaccine lot 052413 with the exception of the antigen.
  Adjuvant (MVP Laboratories, S.O. #25) 100 µL
  Glycerol 100 µL
  Diluent, PBS containing q.s.
  Gentamicin, 30 µg/mL of diluent volume
  Formaldehyde, 0.1% of diluent volume
  Amphotericin B, 2.5 µg/mL Elisa Testing Procedure A direct bind ELISA was established to evaluate the antibody response to vaccination with *Corynebacterium Pseudotuberculosis* Bacterin-Toxoid. Thermo Immulon 4HBX plates (lot ND540611) were coated with a 1:10 dilution of *Corynebacterium pseudotuberculosis* bacterin lot 041913-3X in carbonate buffer overnight at 37° C. Plates were washed and then blocked with 3% Blotto for 1-2 hours at room temperature. Horse sera to be evaluated were serially diluted 2-fold down the plate from 1:10 to 1:640, and plates were then incubated for 2-3 hours at room temperature. Plates were then washed and conjugate (α-horse IgG H+L HRP lot 17446, diluted 1:3000 in Blotto, Rockland Immunochemicals, Inc.) added for 1-2 hours at room temperature. Plates were again washed and substrate (TMB) was added. Plates were stopped after 10-15 minutes by the addition of sulfuric acid and were immediately read at 450/650 nm. Positive and negative control sera were from horses used in previous studies of immune response to *Corynebacterium Pseudotuberculosis* Bacterin-Toxoid.

Blood from these horses was collected for preparation as control sera for the ELISA assay.

Description of Experimental Horses

Forty (40) horses one year of age were used in this study. Horses were selected by random number generator to be either in the Investigative Veterinary Product (IVP) group or in the control product (CP) group. Twenty (20) horses served as IVP vaccinates and 20 horses served as controls. All horses were housed in a single pasture for the entirety of the 42-day serological evaluation.

During the entire vaccination/serology study, horses were quartered in a single pasture with common feed bunks, waterers and hay racks. During each vaccination and blood-draw day, horses were corralled into holding pens and worked randomly through individual restraining chutes. Table 1 summarizes the study design:

TABLE 1

Study Design

| Group | No. Test Animals | Treatment | Doses (21 day intervals) | Route of Administration |
|---|---|---|---|---|
| 1 | 20 | IVP | 2 × 1 mL | IM |
| 2 | 20 | CP | 2 × 1 mL | IM |

Masking/Bias Reducing Methods

In order to avoid bias, IVP and control vaccine for the study horses was drawn out into unlabeled 3 cc syringes of identical appearance, kept in separate groupings, and given to the barn manager for appropriate handling to assure blinding of the personnel giving the vaccine. Because the vaccine in this study does not contain phenol red, the IVP and control product appear identical. The assistant read the microchip number of each horse and identified the appropriate product for immunization while a veterinarian took blood from the animal. Once the blood was collected, an assistant handed the veterinarian the correct product in the 3 cc syringe for immunization of the animal according to treatment assignment. The veterinarian did not have knowledge of which product was given to any animal during the immunization timeframe. The veterinarian and laboratory personnel were additionally blinded to microchip numbers and treatment group assignment throughout the entire study.

Vaccination and Sampling Schedule

On Day 0 and Day 21, the immunological composition of the present invention was administered intramuscularly in a 1 mL dose volume to each of 20 horses. Twenty (20) horses received a 1 mL dose of adjuvanted media (CP lot 052413-Neg) containing excipients used in the IVP vaccine (adjuvant, glycerol, gentamicin, formaldehyde and amphotericin B). Blood was taken from each horse for evaluation of antibody on Study Days 0, 7, 21, 28, 35 and 42. The Vaccination and Sampling Schedule Table 2 is provided below:

TABLE 2

Vaccination and Sampling Schedule

| Study Day | Study Event |
|---|---|
| 0 | Randomize horses to groups |
| | Collected serum samples all horses |
| | IVP administered to 20 horses |
| | CP administered to 20 horses |
| | General Health Observations all horses |
| 1-6 | General Health Observations all horses |
| 7 | Collected serum samples all horses |
| | General Health Observations all horses |
| 8-20 | General Health Observations all horses |
| 21 | Collected serum samples all horses |
| | IVP administered to 20 horses |
| | CP administered to 20 horses |
| | General Health Observations all horses |
| 22-27 | General Health Observations all horses |
| 28 | Collected serum samples all horses |
| | General Health Observations all horses |
| 29-34 | General Health Observations all horses |
| 35 | Collected serum samples all horses |
| | General Health Observations all horses |
| 36-41 | General Health Observations all horses |
| 42 | Collected serum samples all horses |
| | General Health Observations all horses |
| | Study end |

Results

Sera were tested by a single operator to exclude any variability in the assay (with the exception of the day to day or plate to plate variability). Sera from each study day were evaluated in an identical manner and the 1:80 dilution of serum on the plate was chosen for interpretation of results for this report. A cut-off value of 0.5 OD was chosen as an indicator of antibody to *Corynebacterium pseudotuberculosis* based on data from prior studies during ELISA development. Eighteen of 20 horses immunized with the IVP vaccine developed high titers to *Corynebacterium pseudotuberculosis* antigen within 14 days of the post-booster vaccination. Control horses remained negative throughout the trial.

Results are listed in the Tables 3-9 and shown in the Figs.

TABLE 3

Day 0 (pre-vaccination) Antibody Response to *C. pseudotuberculosis*

| Laboratory Number | Horse ID | Treatment Group | Optical Density (1:80 Serum Dilution) |
|---|---|---|---|
| 2 | 74099830 | CP | 0.394 |
| 3 | 74102319 | CP | 0 |
| 4 | 74102830 | CP | 0.061 |
| 5 | 74103001 | CP | 0.069 |
| 6 | 74104285 | CP | 0.133 |
| 8 | 74104114 | CP | 0.048 |
| 9 | 74104841 | CP | 0.094 |
| 12 | 74106116 | CP | 0.125 |
| 15 | 74108535 | CP | 0.12 |
| 16 | 74109821 | CP | 0.28 |
| 17 | 74110028 | CP | 0.19 |
| 18 | 74110869 | CP | 0.203 |
| 19 | 74113046 | CP | 0.186 |
| 24 | 74121258 | CP | 0.132 |
| 28 | 74124801 | CP | 0.235 |
| 29 | 74125109 | CP | 0.22 |
| 30 | 74795840 | CP | 0.21 |

TABLE 3-continued

Day 0 (pre-vaccination) Antibody Response to *C. pseudotuberculosis*

| Laboratory Number | Horse ID | Treatment Group | Optical Density (1:80 Serum Dilution) |
|---|---|---|---|
| 33 | 75066513 | CP | 0.149 |
| 34 | 75068009 | CP | 0.226 |
| 37 | 75087292 | CP | 0.128 |
| 1 | 74099549 | IVP | 0.079 |
| 7 | 74104338 | IVP | 0.126 |
| 10 | 74106041 | IVP | 0.139 |
| 11 | 74106069 | IVP | 0.143 |
| 13 | 74108116 | IVP | 0.182 |
| 14 | 74108527 | IVP | 0.111 |
| 20 | 74114870 | IVP | 0.176 |
| 21 | 74117299 | IVP | 0.192 |
| 22 | 74120295 | IVP | 0.102 |
| 23 | 74121119 | IVP | 0.184 |
| 25 | 74123002 | IVP | 0.15 |
| 26 | 74123069 | IVP | 0.205 |
| 27 | 74123543 | IVP | 0.24 |
| 31 | 75046816 | IVP | 0.175 |
| 32 | 75054370 | IVP | 0.157 |
| 35 | 75076544 | IVP | 0.191 |
| 36 | 75078121 | IVP | 0.325 |
| 38 | 75090370 | IVP | 0.326 |
| 39 | 75092868 | IVP | 0.226 |
| 40 | 75096031 | IVP | 0.295 |
| Neg | H23-042913 | NEGATIVE SERUM | 0.204 |
| Pos | H29-042913 | POSITIVE SERUM | 1.726 |

TABLE 4

Day 7 Antibody Response to *C. pseudotuberculosis*

| Laboratory Number | Horse ID | Treatment Group | Optical Density (1:80 Serum Dilution) |
|---|---|---|---|
| 2 | 74099830 | CP | 0.491 |
| 3 | 74102319 | CP | 0.048 |
| 4 | 74102830 | CP | 0.119 |
| 5 | 74103001 | CP | 0.136 |
| 6 | 74104285 | CP | 0.17 |
| 8 | 74104114 | CP | 0.137 |
| 9 | 74104841 | CP | 0.208 |
| 12 | 74106116 | CP | 0.15 |
| 15 | 74108535 | CP | 0.147 |
| 16 | 74109821 | CP | 0.165 |
| 17 | 74110028 | CP | 0.137 |
| 18 | 74110869 | CP | 0.134 |
| 19 | 74113046 | CP | 0.123 |
| 24 | 74121258 | CP | 0.113 |
| 28 | 74124801 | CP | 0.22 |
| 29 | 74125109 | CP | 0.147 |
| 30 | 74795840 | CP | 0.195 |
| 33 | 75066513 | CP | 0.112 |
| 34 | 75068009 | CP | 0.186 |
| 37 | 75087292 | CP | 0.149 |
| 1 | 74099549 | IVP | 0.157 |
| 7 | 74104338 | IVP | 0.203 |
| 10 | 74106041 | IVP | 0.143 |
| 11 | 74106069 | IVP | 0.142 |
| 13 | 74108116 | IVP | 0.216 |
| 14 | 74108527 | IVP | 0.209 |
| 20 | 74114870 | IVP | 0.108 |
| 21 | 74117299 | IVP | 0.178 |
| 22 | 74120295 | IVP | 0.127 |
| 23 | 74121119 | IVP | 0.162 |
| 25 | 74123002 | IVP | 0.141 |
| 26 | 74123069 | IVP | 0.162 |
| 27 | 74123543 | IVP | 0.277 |
| 31 | 75046816 | IVP | 0.155 |

TABLE 4-continued

Day 7 Antibody Response to *C. pseudotuberculosis*

| Laboratory Number | Horse ID | Treatment Group | Optical Density (1:80 Serum Dilution) |
|---|---|---|---|
| 32 | 75054370 | IVP | 0.143 |
| 35 | 75076544 | IVP | 0.162 |
| 36 | 75078121 | IVP | 0.258 |
| 38 | 75090370 | IVP | 0.319 |
| 39 | 75092868 | IVP | 0.225 |
| 40 | 75096031 | IVP | 0.267 |
| Neg | H23-042913 | NEGATIVE SERUM | 0.164 |
| Pos | H29-042913 | POSITIVE SERUM | 1.644 |

TABLE 5

Day 21 (Day of 2$^{nd}$ Vaccination) Antibody Response to *C. pseudotuberculosis*

| Laboratory Number | Horse ID | Treatment Group | Optical Density (1:80 Serum Dilution) |
|---|---|---|---|
| 2 | 74099830 | CP | 0.383 |
| 3 | 74102319 | CP | 0.054 |
| 4 | 74102830 | CP | 0.108 |
| 5 | 74103001 | CP | 0.136 |
| 6 | 74104285 | CP | 0.123 |
| 8 | 74104114 | CP | 0.213 |
| 9 | 74104841 | CP | 0.17 |
| 12 | 74106116 | CP | 0.126 |
| 15 | 74108535 | CP | 0.086 |
| 16 | 74109821 | CP | 0.187 |
| 17 | 74110028 | CP | 0.151 |
| 18 | 74110869 | CP | 0.118 |
| 19 | 74113046 | CP | 0.151 |
| 24 | 74121258 | CP | 0.164 |
| 28 | 74124801 | CP | 0.18 |
| 29 | 74125109 | CP | 0.114 |
| 30 | 74795840 | CP | 0.119 |
| 33 | 75066513 | CP | 0.094 |
| 34 | 75068009 | CP | 0.144 |
| 37 | 75087292 | CP | 0.082 |
| 1 | 74099549 | IVP | 0.267 |
| 7 | 74104338 | IVP | 0.288 |
| 10 | 74106041 | IVP | 0.155 |
| 11 | 74106069 | IVP | 0.218 |
| 13 | 74108116 | IVP | 0.289 |
| 14 | 74108527 | IVP | 0.455 |
| 20 | 74114870 | IVP | 0.226 |
| 21 | 74117299 | IVP | 0.128 |
| 22 | 74120295 | IVP | 0.198 |
| 23 | 74121119 | IVP | 0.133 |
| 25 | 74123002 | IVP | 0.321 |
| 26 | 74123069 | IVP | 0.144 |
| 27 | 74123543 | IVP | 1.011 |
| 31 | 75046816 | IVP | 0.14 |
| 32 | 75054370 | IVP | 0.107 |
| 35 | 75076544 | IVP | 0.109 |
| 36 | 75078121 | IVP | 0.225 |
| 38 | 75090370 | IVP | 0.269 |
| 39 | 75092868 | IVP | 0.137 |
| 40 | 75096031 | IVP | 0.275 |
| Neg | H23-042913 | NEGATIVE SERUM | 0.089 |
| Pos | H29-042913 | POSITIVE SERUM | 1.67 |

TABLE 6

Day 28 (7 Days post-booster vaccination) Antibody Response to *C. pseudotuberculosis*

| Laboratory Number | Horse ID | Treatment Group | Optical Density (1:80 Serum Dilution) |
|---|---|---|---|
| 2 | 74099830 | CP | 0.251 |
| 3 | 74102319 | CP | 0.082 |
| 4 | 74102830 | CP | 0.12 |
| 5 | 74103001 | CP | 0.119 |
| 6 | 74104285 | CP | 0.303 |
| 8 | 74104114 | CP | 0.162 |
| 9 | 74104841 | CP | 0.131 |
| 12 | 74106116 | CP | 0.072 |
| 15 | 74108535 | CP | 0.073 |
| 16 | 74109821 | CP | 0.153 |
| 17 | 74110028 | CP | 0.102 |
| 18 | 74110869 | CP | 0.227 |
| 19 | 74113046 | CP | 0.094 |
| 24 | 74121258 | CP | 0.223 |
| 28 | 74124801 | CP | 0.155 |
| 29 | 74125109 | CP | 0.159 |
| 30 | 74795840 | CP | 0.176 |
| 33 | 75066513 | CP | 0.07 |
| 34 | 75068009 | CP | 0.105 |
| 37 | 75087292 | CP | 0.092 |
| 1 | 74099549 | IVP | 0.263 |
| 7 | 74104338 | IVP | 0.257 |
| 10 | 74106041 | IVP | 0.175 |
| 11 | 74106069 | IVP | 0.126 |
| 13 | 74108116 | IVP | 0.183 |
| 14 | 74108527 | IVP | 0.15 |
| 20 | 74114870 | IVP | 0.159 |
| 21 | 74117299 | IVP | 0.068 |
| 22 | 74120295 | IVP | 0.143 |
| 23 | 74121119 | IVP | 0.147 |
| 25 | 74123002 | IVP | 0.311 |
| 26 | 74123069 | IVP | 0.123 |
| 27 | 74123543 | IVP | 1.088 |
| 31 | 75046816 | IVP | 0.04 |
| 32 | 75054370 | IVP | 0.1 |
| 35 | 75076544 | IVP | 0.14 |
| 36 | 75078121 | IVP | 0.115 |
| 38 | 75090370 | IVP | 0.245 |
| 39 | 75092868 | IVP | 0.151 |
| 40 | 75096031 | IVP | 0.313 |
| Neg | H23-042913 | NEGATIVE SERUM | 0.072 |
| Pos | H29-042913 | POSITIVE SERUM | 1.265 |

TABLE 8

Day 35 (14 Days post-booster vaccination) Antibody Response to *C. pseudotuberculosis*

| Laboratory Number | Horse ID | Treatment Group | Optical Density (1:80 Serum Dilution) |
|---|---|---|---|
| 2 | 74099830 | CP | 0.397 |
| 3 | 74102319 | CP | 0.069 |
| 4 | 74102830 | CP | 0.113 |
| 5 | 74103001 | CP | 0.146 |
| 6 | 74104285 | CP | 0.148 |
| 8 | 74104114 | CP | 0.116 |
| 9 | 74104841 | CP | 0.165 |
| 12 | 74106116 | CP | 0.145 |
| 15 | 74108535 | CP | 0.155 |
| 16 | 74109821 | CP | 0.272 |
| 17 | 74110028 | CP | 0.301 |
| 18 | 74110869 | CP | 0.156 |
| 19 | 74113046 | CP | 0.152 |
| 24 | 74121258 | CP | 0.155 |
| 28 | 74124801 | CP | 0.172 |
| 29 | 74125109 | CP | 0.122 |
| 30 | 74795840 | CP | 0.151 |
| 33 | 75066513 | CP | 0.127 |
| 34 | 75068009 | CP | 0.205 |
| 37 | 75087292 | CP | 0.212 |
| 1 | 74099549 | IVP | 1.565 |
| 7 | 74104338 | IVP | 0.884 |
| 10 | 74106041 | IVP | 1.558 |
| 11 | 74106069 | IVP | 1.218 |
| 13 | 74108116 | IVP | 0.767 |
| 14 | 74108527 | IVP | 1.242 |
| 20 | 74114870 | IVP | 1.307 |
| 21 | 74117299 | IVP | 1.076 |
| 22 | 74120295 | IVP | 0.967 |
| 23 | 74121119 | IVP | 0.906 |
| 25 | 74123002 | IVP | 1.762 |
| 26 | 74123069 | IVP | 0.231 |
| 27 | 74123543 | IVP | 2.061 |
| 31 | 75046816 | IVP | 1.302 |
| 32 | 75054370 | IVP | 0.589 |
| 35 | 75076544 | IVP | 0.171 |
| 36 | 75078121 | IVP | 1.727 |
| 38 | 75090370 | IVP | 1.427 |
| 39 | 75092868 | IVP | 1.197 |
| 40 | 75096031 | IVP | 1.531 |
| Neg | H23-042913 | NEGATIVE SERUM | 0.136 |
| Pos | H29-042913 | POSITIVE SERUM | 1.935 |

TABLE 9

Day 42 (21 Days post-booster vaccination) Antibody Response to *C. pseudotuberculosis*

| Laboratory Number | Horse ID | Treatment Group | Optical Density (1:80 Serum Dilution) |
|---|---|---|---|
| 2 | 74099830 | CP | 0.43 |
| 3 | 74102319 | CP | 0.083 |
| 4 | 74102830 | CP | 0.147 |
| 5 | 74103001 | CP | 0.123 |
| 6 | 74104285 | CP | 0.111 |
| 8 | 74104114 | CP | 0.097 |
| 9 | 74104841 | CP | 0.157 |
| 12 | 74106116 | CP | 0.135 |
| 15 | 74108535 | CP | 0.115 |
| 16 | 74109821 | CP | 0.184 |
| 17 | 74110028 | CP | 0.13 |
| 18 | 74110869 | CP | 0.141 |
| 19 | 74113046 | CP | 0.093 |
| 24 | 74121258 | CP | 0.192 |
| 28 | 74124801 | CP | 0.14 |
| 29 | 74125109 | CP | 0.127 |
| 30 | 74795840 | CP | 0.136 |
| 33 | 75066513 | CP | 0.11 |
| 34 | 75068009 | CP | 0.176 |
| 37 | 75087292 | CP | 0.107 |
| 1 | 74099549 | IVP | 1.031 |
| 7 | 74104338 | IVP | 0.731 |
| 10 | 74106041 | IVP | 0.631 |
| 11 | 74106069 | IVP | 1.233 |
| 13 | 74108116 | IVP | 0.631 |
| 14 | 74108527 | IVP | 1.117 |
| 20 | 74114870 | IVP | 1.166 |
| 21 | 74117299 | IVP | 0.804 |
| 22 | 74120295 | IVP | 1.033 |
| 23 | 74121119 | IVP | 1.173 |
| 25 | 74123002 | IVP | 2.231 |
| 26 | 74123069 | IVP | 0.182 |

TABLE 9-continued

Day 42 (21 Days post-booster vaccination) Antibody
Response to *C. pseudotuberculosis*

| Laboratory Number | Horse ID | Treatment Group | Optical Density (1:80 Serum Dilution) |
|---|---|---|---|
| 27 | 74123543 | IVP | 2.168 |
| 31 | 75046816 | IVP | 1.262 |
| 32 | 75054370 | IVP | 0.619 |
| 35 | 75076544 | IVP | 0.14 |
| 36 | 75078121 | IVP | 1.88 |
| 38 | 75090370 | IVP | 1.535 |
| 39 | 75092868 | IVP | 1.093 |
| 40 | 75096031 | IVP | 1.488 |
| Neg | H23-042913 | NEGATIVE SERUM | 0.186 |
| Pos | H29-042913 | POSITIVE SERUM | 1.806 |

Discussion

This study was designed to demonstrate that vaccination of horses with *Corynebacterium Pseudotuberculosis* Bacterin-Toxoid produced antibody responses to Corynebacterium pseudotuberculosis antigen. A previous report in the literature in sheep suggest that IgG antibody is important in protection from abscesses due to *Corynebacterium pseudotuberculosis* and that vaccination confers protection of sheep against infection with a virulent United Kingdom isolate of *Corynebacterium Pseudotuberculosis* (See, Piontkowski, M. D.; Shivvers, D. W., Journal of the American Veterinary Medical Association 1998 Vol. 212 No. 11 pp. 1765-1768 and Fontaine M C, Baird G, Connor K M, Rudge K, Sales J, Donachie W., Vaccine. 2006 Aug. 14; 24(33-34):5986-96. Epub 2006 May 19).

The assay performed in this study is a direct bind ELISA where each well of a microtiter plate is coated with a constant amount of washed *Corynebacterium pseudotuberculosis* antigen, sera from immunized or control horses are titrated down the plate, and horse response to vaccination evaluated using a conjugate that detects horse antibody and a substrate which provides color to the reaction. The more dilute the serum that can detect antigen, the higher the serum titer is to that antigen.

Eighteen of 20 horses in this study seroconverted with a high antibody response (≥1:80) to vaccination by Day 35 (14 days post-booster vaccination). All control horses remained seronegative (defined as an Optical Density <0.5 in this assay). These results show that vaccination with 2 doses of *Corynebacterium Pseudotuberculosis* Bacterin-Toxoid (unlicensed, Product Code 7A94.01) results in antibody response in 90% of vaccinated horses that can lead to protection against infection2 with *Corynebacterium pseudotuberculosis*.

These data provide evidence that horses immunized with a 2 dose regimen of *Corynebacterium Pseudotuberculosis* Bacterin-Toxoid given in a 21 day interval between doses, produce high-titered antibody to *Corynebacterium pseudotuberculosis* which is important in protection from abscesses due to *Corynebacterium pseudotuberculosis* infection. The data from this study demonstrates efficacy.

Example 4

Objectives

The objective of this study is to evaluate the six (6) month Duration of Immunity (DOI) of a *Corynebacterium Pseudotuberculosis* Bacterin-Toxoid vaccine. The objective is for the immunization of horses four (4) months of age or older against clinical disease caused by *Corynebacterium pseudotuberculosis*. In this study, horses of 4 months of age or older will be vaccinated with 2 doses of vaccine, 3 weeks apart and challenged a minimum of six (6) months post-booster.

Criteria for Satisfactory Completion of Objectives

The primary parameter to satisfy the study objective will be a mitigated fraction indicating that the vaccine group as compared to the control group experiences reduced occurrence, severity, and/or duration of clinical signs of "pigeon fever" as assessed by the parameters of post-challenge clinical evaluation. Supportive efficacy parameters that will be measured include serum neutralization titers to *C. pseudotuberculosis* and to the phospholipase D toxin associated with virulence of the organism. Reduction of the occurrence, severity and/or duration of disease will confirm efficacy of the vaccine.

Schedule of Events

Pre-screen potential test animals by ELISA for negative status to *C. pseudotuberculosis* cellular antigen and phospholipase D antigen. This study will follow the efficacy protocol described in Example 3, except that the study will end after a minimum of 6 months post booster. Study will end with abatement of clinical signs in all horses. Abatement of clinical signs will be defined as either: 1) complete reduction of clinical signs of disease, where no evidence of prior disease remains, or 2) reduction of clinical disease where no further evidence of remission can be determined by daily examination.

Example 5

Scope

This assay is designed to detect and quantify toxoided phospholipase D in serials of *Corynebacterium pseudotuberculosis*.

Method

Stock Solution Preparation

Amplex Red Stock Solution: Allow one vial of Amplex Red reagent and DMSO to warm to room temperature (18-25° C.). Just prior to use, dissolve contents of the vial of Amplex Red reagent in 100 μL DMSO and vortex thoroughly (10-15 seconds). Stock solution should be protected from light and stored at ≤−20° C. if not used immediately.

Reaction Buffer: Prepare a 1× working solution of Reaction Buffer by adding 5 mL of 5× Reaction Buffer stock solutions) to 20 mL of deionized water (dH2O).

Horseradish Peroxidase Stock Solution: Prepare a 200 U/mL stock solution of horseradish peroxidase (HRP) by dissolving the contents of the vial of HRP in 1.0 mL of 1× Reaction Buffer. After use, the remaining solution should be stored frozen at ≤−20° C.

Hydrogen Peroxide Positive Control: Prepare a ~20 mM H2O2 working solution by diluting 20 μL of the ~3% H2O2 stock solution (from kit) in 980 μL dH2O.

Choline Oxidase Stock Solution: Prepare a 20 U/mL stock solution of choline oxidase by dissolving the contents of the vial of choline oxidase (from kit) in 600 μL of 1× Reaction Buffer. After use, the remaining solution should be stored frozen at ≤−20° C.

PLD Positive Control: Prepare stock solutions of PLD by diluting PLD Streptomyces chromofuscus 2-fold into dH2O to achieve the following approximate stock solution concentrations: 1500 mu/mL; 750 mu/mL; 375 mu/mL; 187.5 mu/mL; 93.75 mu/mL; 46.88 mu/mL; 23.44 mu/mL; 11.72 mu/mL.

Phospholipase D (PLD) Quantification Assay:

The following protocol describes the assay of PLD in a total volume of 200 μL per microplate well. The volumes described here are sufficient for ~100 assays.

Dilute the PLD containing samples in dH2O such that a 2-fold serial dilution is achieved spanning the 8-well length of the plate (i.e., 1:1 through 1:128). A volume of 100 μL will be used for each reaction. Less than 8 dilutions may be used to accommodate more samples per plate. Pipet 100 μL of each PLD positive control dilution into separate wells of a microplate, in triplicate. Pipet 100 μL of each sample/sample dilution into separate wells of a microplate, in triplicate. Pipet 100 μL of reaction buffer into separate wells of a microplate, in triplicate, to serve as a negative control. Pipet 100 μL of $H_2O_2$ positive control into separate wells of a microplate, in triplicate.

(35-40° C.) for 2-3 hours. Keep the drawer closed at all times to maintain temperature and protect the reaction(s) from light. Measure the fluorescence using excitation wavelength of 530 nm and detection wavelength of 590 nm. For each point, correct for background fluorescence by subtracting the values derived from the reaction buffer (no PLD) negative control(s).

Data Analysis

For all controls/samples, the average of the three technical replicates should be used. PLD levels are calculated by the following equation ($R2=0.9845$) relating background corrected relative fluorescence (y) to mU/mL of PLD (x). This equation resulted from the original efficacy serial used to vaccinate horses as described in the Examples above.

$$y=10682*\ln(x)-45003$$

Using the above equation, for each sample, calculate the PLD concentration based on its average fluorescence units (average obtained by averaging technical replicates). Based on the dilution factor of each sample, calculate the dilution factor adjusted PLD level for each dilution of each sample. The average of 3 of the closest PLD calculations should be

TABLE 10

Sample Plate Layout

| | 1 | 2 | 3 | 4 | 5 | 6 | 7 | 8 | 9 | 10 | 11 | 12 |
|---|---|---|---|---|---|---|---|---|---|---|---|---|
| A | PLD Positive Control 1500 mu/mL | PLD Positive Control 1500 mu/mL | PLD Positive Control 1500 mu/mL | | Sample A 1:1 | Sample A 1:1 | Sample A 1:1 | | H2O2 Positive Control | H2O2 Positive Control | H2O2 Positive Control | |
| B | PLD Positive Control 750 mu/mL | PLD Positive Control 750 mu/mL | PLD Positive Control 750 mu/mL | | Sample A 1:2 | Sample A 1:2 | Sample A 1:2 | | | | | |
| C | PLD Positive Control 375 mu/mL | PLD Positive Control 375 mu/mL | PLD Positive Control 375 mu/mL | | Sample A 1:4 | Sample A 1:4 | Sample A 1:4 | | Reaction Buffer Negative Control | Reaction Buffer Negative Control | Reaction Buffer Negative Control | |
| D | PLD Positive Control 187.5 mu/mL | PLD Positive Control 187.5 mu/mL | PLD Positive Control 187.5 mu/mL | | Sample A 1:8 | Sample A 1:8 | Sample A 1:8 | | | | | |
| E | PLD Positive Control 93.75 mu/mL | PLD Positive Control 93.75 mu/mL | PLD Positive Control 93.75 mu/mL | | Sample A 1:16 | Sample A 1:16 | Sample A 1:16 | | | | | |
| F | PLD Positive Control 46.88 mu/mL | PLD Positive Control 46.88 mu/mL | PLD Positive Control 46.88 mu/mL | | Sample A 1:32 | Sample A 1:32 | Sample A 1:32 | | | | | |
| G | PLD Positive Control 23.44 mu/mL | PLD Positive Control 23.44 mu/mL | PLD Positive Control 23.44 mu/mL | | Sample A 1:64 | Sample A 1:64 | Sample A 1:64 | | | | | |
| H | PLD Positive Control 11.72 mu/mL | PLD Positive Control 11.72 mu/mL | PLD Positive Control 11.72 mu/mL | | Sample A 1:128 | Sample A 1:128 | Sample A 1:128 | | | | | |

Prepare a working solution of PLD assay mix by combining the following in a 50 mL conical tube and vortexing briefly:

9.65 mL 1× Reaction Buffer
100 μL Amplex Red stock solution
100 μL HRP stock solution
100 μL choline oxidase stock solution
50 μL lecithin stock solution Immediately pipette 100 μL of PLD assay mix into each microplate well containing a sample/control. Final reaction volume is 200 μL per well. Place the microplate into the pre-heated (35-40° C.) Spectramax Gemini reader.

Figure 7:
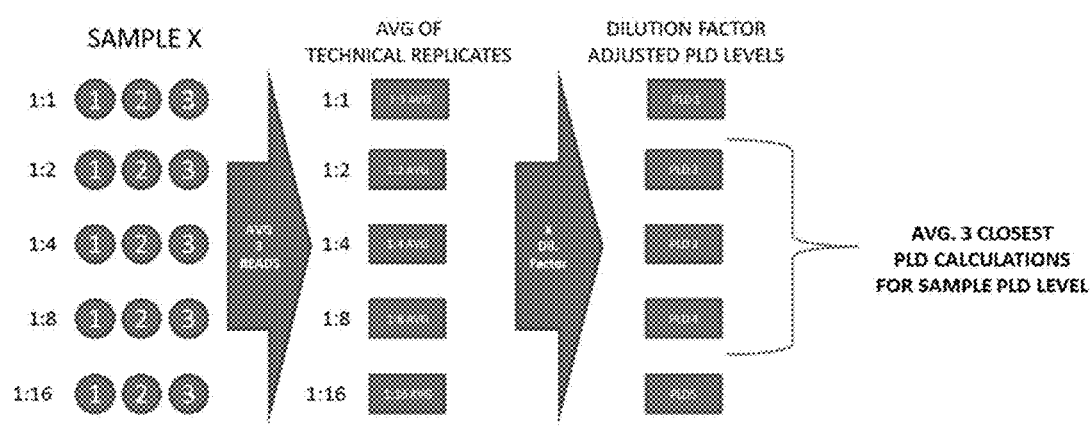
FIG. 7 is a graphical representation of the PLD Calculation Method described in Example 5.

Mix the plate briefly (3-5 seconds) by instructing the Spectramax Gemini to mix the plate via shaking. Close the Spectramax Gemini drawer, and allow plate to incubate at used for each sample (see diagram below). Standard error should also be calculated for informative purposes. FIG. 7 shows a graphical representation of the calculation process.

A successful assay will show $H_2O_2$ positive control with an average fluorescence of >20,000 RFU and an average fluorescence of <100 RFU reaction buffer negative control.

To pass, and show presence of PLD, the average of 3 dilution factor adjusted PLD levels should be ≥328 mU/mL (PLD level of efficacy serial). If failure occurs, two independent re-tests must be performed and pass to confirm satisfactory PLD levels.

Table 11 shows the results of the PLD Assay discussed above.

TABLE 11

PLD Assay results.

| Dilution (1:X) | Read1 | Read2 | Read3 | Avg | StdDev | mU/mL | DilAdj_Conc |
|---|---|---|---|---|---|---|---|
| 1 | −697.079 | −220.352 | 789.3107 | −42.707 | 619.6812 | 67.28767 | 67.28767363 |
| 2 | −373.834 | 853.2247 | 2015.983 | 831.791 | 975.7564 | 73.02805 | 146.0560934 |
| 4 | 2002.214 | 1882.613 | 562.1727 | 1482.333 | 652.4811 | 77.61373 | 310.4549174 |
| 8 | 1110.16 | −135.426 | −385.272 | 196.487 | 654.0663 | 68.81139 | 550.4911361 |
| 16 | −116.478 | −208.525 | −175.854 | −166.953 | 38.10155 | 66.50956 | 1064.15302 |
| 32 | −77.1453 | −210.346 | −155.457 | −147.65 | 54.65862 | 66.62986 | 2132.155491 |
| 64 | 32.23867 | −327.585 | −317.269 | −204.205 | 167.2442 | 66.27802 | 4241.793322 |
| 128 | −248.426 | −228.909 | 87.10667 | −130.076 | 153.7781 | 66.73956 | 8542.664245 |
| AVG CONC | 336 | | | | | | |

| | Read1 | Read2 | Read3 |
|---|---|---|---|
| | Negative Reaction Buffer | | |
| AVG | −6.50633 | 20.84167 | −14.3353 |
| RFU | 3.33E−07 | | |
| | H2O2 Pos. Ctrl | | |
| AVG | 27388.16 | 27562.31 | 27160.55467 |
| RFU | 27370.34 | | |

Example 6

Objective

The objective of this study was to develop a genotyping based isolate identification method. Ten isolate's genomic sequences were evaluated to identify 10 SNPs that allow for the differentiation of one isolate from the remaining isolates. Various techniques may be used including Stefanska et al, Evaluation of Three Methods for DNA Fingerprinting of *Corynebacterium pseudotuberculosis* Strains Isolated from Goats in Poland, Polish J of Microbiology, 2008, Vol. 57, No 2, 105-112, hereby incorporated by reference.

For each SNP, 4 primers were designed that allow for the easy differentiation between alleles on a gel following PCR (1,1-1.5 fold product size difference). The primers and genomic sequences through an in-silico PCR program to verify that only 2 PCR products are generated for each sample (one non-specific, one allele-specific). The source organism and locations are as follows:

C231 (sheep/Brazil)
PAT10 (sheep/Argentina)
267 (llama/USA_UCDavis)
P54B96 (wildebeest/South Africa)
119 (cow/Israel)
3/99-5 (sheep/Scotland)
1002 (goat/Brazil)
FRC41 (human/Germany)
31 (buffalo/Egypt)
316 (horse/USA_CA)

SNP Identification:

To identify the strain of a given sample, SNPs were identified using available reference sequences from NCBI. A total of 10 strains of *Corynebacterium pseudotuberculosis* were consulted from the above listing. Using the genomic sequences for these 10 isolates, SNPs were identified using SNPs Discovery by the Biodefense Informatics division of the Los Alamos National Laboratory. Using discovered SNPs to differentiate isolates, a total of 10 SNPs were required to distinguish any given strain from the remaining strains.

PCR-Based Identification

To differentiate between alleles of a given SNP, a Tetra-primer ARMS-PCR method was used. This method utilizes 4 primers for a given SNP. Two primers (1 forward, 1 reverse) target sequence flanking the SNP and will produce a PCR product in any strain tested. Two additional primers are designed, one corresponding to the first allele (forward primer), the other to the second (reverse primer). These allele specific primers result in allele specific PCR products of different sizes.

For bacterial template DNA, each strain will produce 2 PCR products, one general product, and one allele specific. For each of the 10 SNPs, four primers were designed. These primer sequences were then used in an in-silico reaction to determine if proper amplification will occur. Each strain's genomic sequence was queried for each set of primers for each SNP, with no non-specific PCR products being generated, and all PCR products corresponding to the correct SNP allele as determined by sequence analysis.

Example 7

Objective

The objective of this study is to develop a cptb direct binding ELISA using Bel-D3 ascites as the detector.

Antigen Preparation/Extraction:

Freeze an aliquot of the test antigen(s) at −70° C. or below for a minimum of 18 hours. Place the thawed aliquot(s) at 56° C. for a minimum of 18 to a maximum of 48 hours.

Test Plate Protocol:

Antigen addition, dilution, and incubation on the plate:

Add 100 μL of 0.05M carbonate buffer, pH 9.6, to all 96 wells of the test plate using a 12-channel micropipetor.

Add 100 μL of extracted antigen, in duplicate, to designated wells in the "B" row of the test plate effecting an antigen dilution of 1:2 in the wells.

From the "B" row wells withdraw 100 μL into 12 micropipette tips seated on a 12-channel micropipetor and gently mix within the wells 5-10 times.

Transfer 100 μL of the mixed antigen from the "B" wells to the "C" wells and mix again.

Continue in this manner mixing 2-fold down the test plate for a final antigen dilution of 1:128. Discard the extra 100 μL mixed antigen after mixing in the "H" row.

Seal the plate and incubate at 4° C. on a shaker for a minimum of 18 to a maximum of 24 hours.

Block: Remove plate sealer and discard the antigen liquid into the sink, blot the residual liquid onto a paper towel but don't rinse the wells. Add 100 μL of 5% non-fat-dry-milk in PBS+0.05% tween 20 (PBST) to all wells of the test plate, seal, and incubate at room temperature (22-26° C.) on a shaker for 1-2 hours.

Detector: Dilute purified ascites made from anti-cptb hybridoma clone Bel-D3 (recognizes a 150 kDa MW band in a Western blot) 1:2000 in 1% non-fat-dry-milk diluted in PBST. Remove the plate sealer and discard the blocking liquid into the sink. Rinse each well 3 to 5 times using PBST to fill the wells. Add 100 μL diluted Detector antibody to all wells of the plate. Seal the plate and incubate at room temperature on a shaker overnight for a minimum of 18 to a maximum of 24 hours.

Conjugate: Dilute anti-mouse IgG Fc HRP conjugate 1:3000 in 1% non-fat-dry-milk diluted in PBST. Remove plate sealer and discard the Detector antibody liquid into the sink. Rinse each well 3 to 5 times using PBST to fill the wells. Add 100 μL diluted conjugate to all wells of the plate. Seal the plate and incubate at room temperature on a shaker for 1 to 2 hours.

Substrate: At least 15-30 minutes prior to substrate addition prepare the TMB solution per manufacturer's instructions. Remove plate sealer and discard the conjugate liquid into the sink. Rinse each well 3 to 5 times using PBST to fill the wells. Add 100 μL of TMB substrate to all wells of the plate. Incubate at room temperature on a shaker for 15 to 30 minutes, or until the optical density within the "B" wells reaches the desired dense blue value.

Stop solution: Add 30 μL of 1.5M sulfuric acid to each well containing the TMB substrate. The well color will change to various shades of yellow.

Read: Read the Optical Density (OD) on a microplate reader at a setting of 450 nm-650 nm and calculate relative potency based on declining ODs of the test sample compared to those of a reference standard. The reference standard set of OD's equals a value of "1" and the test sample will either be less concentrated, the same as, or more concentrated as the reference based upon the ODs presented by the test sample.

What is claimed is:

1. An immunogenic composition of one or more isolates of inactivated *Corynebacterium Pseudotuberculosis* isolate deposited with the ATCC under Accession no. PTA-121358.

2. The immunogenic composition of claim 1 in which the isolate, prior to inactivation, grows in cell culture to at least $10^8$ CFU/mL.

3. The immunogenic composition according to claim 1, wherein any of the isolates are present in an amount from about $10^{2.0}$ CFU/mL-$10^{8.0}$ CFU/mL per dose.

4. The immunogenic composition according to claim 1, wherein said immunogenic composition further comprises a suitable pharmaceutical carrier.

5. The immunogenic composition according to claim 4, wherein said suitable pharmaceutical carrier is selected from the group consisting of a diluent, a carbomer adjuvant, antimicrobial agent, preservative, inactivating agent, and combinations thereof.

6. A method for reducing the incidence or lessening the severity of clinical symptoms associated with or caused by *Corynebacterium pseudotuberculosis* in horses or a herd of horses, comprising the step of administering the immunogenic composition according to claim 1 to a horse or herd of horses in need thereof.

7. The method according to claim 6, wherein any of the isolates are present in an amount from about $10^6$ CFU/mL-$10^{11}$ CFU/mL per dose for bacterium.

8. The method according to claim 6, wherein said immunogenic composition further comprises a suitable pharmaceutical carrier.

9. The method according to claim 8, wherein said suitable pharmaceutical carrier is selected from the group consisting of a diluent, a carbomer adjuvant, antimicrobial agent, preservative, inactivating agent, and combinations thereof.

10. The method according to claim 9, wherein said immunogenic composition is administered in one or more doses.

11. The method according to claim 10, wherein one dose of said immunogenic composition is formulated in a dosage form of 0.5 mL to 2.5 mL.

12. The method according to claim 9, wherein said immunogenic composition is safe for use in foals or horses 4 months of age or older.

13. A method for producing an immunogenic composition comprising one or more isolates of inactivated *Corynebacterium Pseudotuberculosis*, the method comprising:

a) growing a virulent *Corynebacterium pseudotuberculosis* organism in growth media which allows high CFU/ mL titer and high Phospholipase D production by the virulent *Corynebacterium pseudotuberculosis* organism;

b) harvesting the organism, phospholipase D and media;

c) contacting the organism, phospholipase D, and media culture with an inactivating agent to obtain the inactivated *Corynebacterium Pseudotuberculosis* Bacterin-Toxoid, d) filtering the inactivated culture in said media to yield a substantially purified *Corynebacterium Pseudotuberculosis* organism and phospholipase D toxoid; and e) said *Corynebacterium pseudotuberculosis* isolate is ATCC Accession No. PTA-121358.

14. An immunogenic composition comprising a *Corynebacterium pseudotuberculosis* isolate having ATCC Accession No. PTA-121358 and Amphotericin B, gentamicin sulfate, formaldehyde, and an adjuvant.

15. The method of claim 13 further comprising adding an adjuvant and one or more preservatives.

* * * * *

SEQUENCE LISTING

```
<160> NUMBER OF SEQ ID NOS: 14

<210> SEQ ID NO 1
<211> LENGTH: 353
<212> TYPE: DNA
<213> ORGANISM: Equine rhinitis A virus

<400> SEQUENCE: 1
atgcctgtag cgtcagtaaa acgcggtaaa cataggcttt gactgtagcg tcagtaaaac      60
gcaacaacca tacgctgttg tgcctgtagc gtcagtaaaa cgcggcaaac gcaagcatta     120
actgtagcgt cagtaaaacg caacaaccat acgctaatgt gcctgaggcg tcagtaaacg     180
catacagcaa accagagctt cccggcttta agggttactg ctcgtaatga gagcacttgg     240
caatttgtca ggatttcctg gtggttgtca cgggagagag gagcccgttt tcgggcactg     300
ttcccaacaa acatttgtgc gcttcggcgc acacccgct cagcccctg tca             353

<210> SEQ ID NO 2
<211> LENGTH: 7839
<212> TYPE: DNA
<213> ORGANISM: Equine rhinitis A virus

<400> SEQUENCE: 2 ttctttttt tcccttccc tcgatcaccg acgttggggg gggggggtt gaaaaagttt         60 atgcctgtag cgtcagtaaa acgcggtaaa cataggcttt gactgtagcg tcagtaaaac     120
gcaacaacca tacgctgttg tgcctgtagc gtcagtaaaa cgcggcaaac gcaagcatta     180
actgtagcgt cagtaaaacg caacaaccat acgctaatgt gcctgaggcg tcagtaaacg     240
catacagcaa accagagctt cccggcttta agggttactg ctcgtaatga gagcacttgg     300
caatttgtca ggatttcctg gtggttgtca cgggagagag gagcccgttt tcgggcactg     360
ttcccaacaa acatttgtgc gcttcggcgc acacccgct cagcccctg tcattgactg       420 gtcgaaggcg ctcgcaataa gactggtcgt cacttggctt ttctatccgt tcaggcttta     480
gcgcgccctc gcgcggcggg ttgtcaggcc cgtgtgctgt acagcaccag gtaaccggac     540
agcagcttgc tggattttcc cggtgccatt gctctggatg gtgtcaccaa gctggtggat     600
```

```
gaagagtgaa cctgatgaag caacacactt gtggtagcgc tgcccaaaag ggagcggaat    660
tcccccgccg cgaggcggtc ctctctggcc aaaagcccag cgttaatagc gccttttggg    720
atgcaggtac cccacctgcc aagtgtgaag tggaatcagc ggatctctga ttcggcctgt    780
actgaactac accatctacc gctgtgaaga atgtcctgaa ggcaagctgg ttacagccct    840
gatcaggagc cccatccatg actctcgatt ggcatggggt caaaaattgt ctaagcagcg    900
gcagggacgc gggagcgttt cctttccatt ttgatttgca tgatggcggc gtctaaagtg    960
tacagggttt gcgagcagac tcttctcgct ggcgccgtgc gcatgatgga caagttttg    1020 cagaagagag ttgttttttgt gccacaccta gataaacagg tacgcctgac aggtcttcac   1080
aactatgaca acacatgttg gcttaatgcc ttgactcagt tgactcagat tcttggaatt   1140 cggcttttg atgaacactt tggaaacaga ggtttgttca ctcggaaaac aattgattgg   1200
gtgagtgacc aaactggaat aaaggattta aaatcaggag cgccacccct cgtggtggtt   1260
tacaagctct ggcaacacgg ccatttggat gtcggcacca tggaaaagcc cagaccaatc   1320
acgctttggt ctgggcccaa agtgtgtctg tctgacatgt gggcgtgtgt ttctgccaag   1380
cctggacacg cagtgttcta tctcttgact gatgaaggat ggatttgcat tgatgacaag   1440
aaaatttatt atgaaacacc agagcccgac gatgtcttgg tcttcgcacc ctatgatttt   1500
gagtcactcg gaaaagatcc tcctaggctg caccaaagat acgaaaaggc tttcaaaaag   1560
ttgtcaggag ctgggacctc tactccgaca accgggaatc agaatatgtc gggcaatagt   1620
gggtccattg tccaaaattt ttacatgcaa caataccaaa attcaattga tgcagacctg   1680
ggcgataatg tcatcagtcc tgaaggccaa ggcagcaaca ctagtagctc tacctcctca   1740
agccagtcgt ctggtttagg tggatggttc tctagtctgc tcaacctagg taccaagcta   1800
ctggctgaca aaaagacaga agaaaccaca acattgagg acaggattga acaacagtt    1860 gtgggagtga cgattatcaa ttcacaaggg tcagttggca caacctattg ttactccaag   1920
cctgacagca agcgccctc cacagtgtct gacccggtca cccggctggg gccaactctt   1980
tctagacact acaccttcaa ggttggagag tggccacact cacaatccca tgggcacgcc   2040
tggatttgcc cactgcccgg ggacaaactt aaaaagatgg gcagtttcca cgaggtggtg   2100
aaggcacacc acttggtgaa gaatggatgg gatgtggttg ttcaggtgaa tgcctctttt   2160
gcccactcgg gagctctttg cgttgcagca gttcctgagt atgaacacac ccatgagaag   2220
gctctaaaat ggtctgagct tgaagaacct gcttatacat atcagcagct ttcagtgttt   2280
ccacatcaat tgttaaattt gagaacaaat tcttctgtac acttggttat gccctatatt   2340
ggacctgggc caaccacgaa tttgacactt cataacccct ggaccattgt aatcttgatt   2400
ttgtctgaac tgcagggcc tggccagact gtgcccgtca ccatgtcggt ggctcctatt   2460
gacgccatgg tgaatgggcc tctcccaaac ccagaggcac caattagagt ggtttcagta   2520
cctgagtcag attcgttcat gtcttctgtg ccagacaatt ctaccccgct ttatccaaag   2580
gttgtggtcc ccctcggca agtcccaggg aggttcacga atttattga tgtggctaaa   2640 cagacttact cattttgctc catctctggc aagccctatt ttgaggtgac aaatacttca   2700
ggagacgagc ctctgtttca gatggatgtc tccctcagtg ctgctgagtt gcacgggaca   2760
tatgttgcaa gcttgtcatc tttctttgca cagtacaggg gttcactaaa cttcaatttc   2820
atcttcactg gagctgcggc aaccaaagct aaattcttgg tcgccttcgt tcctccccac   2880
acagccgcgc ctaaaacgcg ggatgaagcc atggcgtgta tacacgcagt gtgggatgtc   2940
```

```
ggcttgaatt ctgcctttc tttcaatgtg ccttattcat ctccagctga ctttatggcc    3000
gtttactcgg cagaggcaac ggttgtgaat gtgtctggct ggctacaagt ttatgccttg    3060
actgctctca cttcaactga cattgctgtg aatagcaagg gccgtgtttt ggtggccgtt    3120
tctgctgggc cagatttctc acttcgacac cccgtggatc tgcctgacaa gcaggtcaca    3180
aatgtgggcg aggacgggga accaggtgaa actgagcccc gttatgctct gtctccagtg    3240
gacatgcatg ttcatacgga tgtcagcttc ctgctagaca gatttttga tgttgaaaca    3300 attgagcttt caaatttgac tgggtcacca accactcata ttttgaaccc atttggctcc    3360
accgctcagt tggcatgggc taggctgttg aacacctgca catatttctt ttcaaatttg    3420
gagttgtcta tacaattcaa atttacaaca atgccctctt ccgttgaaaa aggcttcgtc    3480
tgggttaagt ggttcccggt tggagcacca acaaaaacaa cagatgcatg gcagcttgaa    3540
ggcggaggca actccgtcag aattcaaaaa ctggctgtgg ctggcctctc acccaccgtt    3600
atttttaaaa ttgctggctc gcggtcgcag gcatgtggct tcaatgtgcc ctacacttca    3660
atgtggcggg ttgtgccagt cttttacaac ggttggggcg cgcccacaaa agagaaagca    3720
acctacaatt ggcttccggg cgcacatttt gggtcgatac ttttgacttc tgatgcacac    3780
gacaagggtg gctgttacct gcggtatcga ttcccgcggg ctagcatgta ctgcccaaga    3840
cctattccgc ccgcattcac ccggccggcg gataagacta ggcacaaatt ccctacaaac    3900
attaacaaac agtgcactaa ttatgccctt cttaaattgg caggtgatgt agagagtaat    3960
cctggcccca ctattttc taaagcttct gctgatttga acgccctgtc cacctctctt    4020
ggtgagttga ctggtatgct taaggatttg aaagctaagg ctgaaactta ttccccctt    4080 tataaaatgg caaaaatgtt gtttaaattg gccactctag cggttgccgc tatgagaaca    4140
aaagacccag ttgtagtggt gatgttgata gctgattttg gattggaagt tttgatacg    4200 ggtttcttct tctcgtattt tcaagagaaa ctgcagcctt atatgaagac cattcccggc    4260
aaagtttctg atttggttac agacgcagct actgctgcag ctcaaattcc aaaaggggtg    4320
tattcttttg tgtcatcttt cttttgagaca ccagaaggtg tggttgagaa acaggttct    4380 cttaggacta tcaatgatat ttttactctc ttgaaaaatt cggactggtt tattaagacg    4440
ctggttgctc tcaaaaagtg gctggtgtcg tggttcaaac aggaacagca agcagatgat    4500 gcccttat ctgaattgga aaaataccct ttgtataaat tgaaattgaa ggaaccagac    4560
actcaggagg aggcccgcca gtggttcaaa gacatgcagc agagagcctt ggcagtgaag    4620
gataagggtt tattctctct gttgcaaatc cctcttgtga acttgcctac atcacgtcct    4680
gaacccgttg tgtgtgtgct gagaggcgcg tccggacagg gcaagtccta tttagcaaac    4740
atgatggctc aggctatttc tcttctccta actgggaaac agaacagtgt gtggagttgc    4800
ccacccgacc ccacatactt tgatggttat aacggacaag ctgttgtcat aatggatgac    4860
ttgggccaaa accctaacgg agcagatttc aagtatttct gtcagatggt gtcaactaca    4920
gcctttgttc caccaatggc ccacttggat gacaagggaa ttccctttac ctctcctgtt    4980
gttatttgta ctacaaattt gcattcctct ttcaccccaa ttactgtgtc atgtcctgag    5040
gctctgaaaa gaaggttccg gtttgacgtg actgtttctg ctaagcctgg ttttgtgagg    5100
actgtggggt cgtctcagct tttgaacttg cctcttgctt tgaagcctgc tggtcttcca    5160
cctcatccta tttttgagaa tgacatgccc attttgaatg gtcaggctgt gaaattggct    5220
ttgtcaggtg ttgaagtgac cgcctttgag ttaattgaga tgattttgtc tgaggtgcag    5280
aatagacagg acacacacaa gatgcctatt tttaaacagt cctggtctga tttgttcaag    5340
```

-continued

```
aagtgtacaa gtgatgagga acagaagatg ttgcagtttc tgattgatca caaggattct    5400
gaaattttga aggcgtttgt ttcagagcgc tctattatgc tgcatgaaga gtacatgaaa    5460
tgggagtctt atatgaccag aagggccaag tatcatcgct tggcggcaga ttttgctatg    5520
ttcttgtcta ttcttacatc attgattgtt atttttgct tggtgtattc tatgtatcag     5580
cttttcaaaa ctccagatga gcattcggct tatgacccag caaccaaacc aaagcccaag    5640
acacaggaaa ttaagacact aaagattcgc acagaaacag gcgtgcctgc cacagacctg    5700
cagcagtccg tgatgaaaaa tgttcagcca attgagttgt actgtgaggg taatctggtt    5760
actgactgct cagcactggg tgtttatgac aactcctact tggtaccttt acatttgttt    5820
gagtttgatt ttgacaccat tgtgctgggc gggcgccagt atagcaaggc agactgtgag    5880
aaggttgagt ttgagctcag cgtcggaggg gacatggtgt cgtctgatgc ctgtctgctt    5940
cgactccctt cgggtcccaa agttagaaac atacttcatt tgtttaccaa tgaaattgag    6000
ctcaaaaaga tgacccaaat tacaggaatt atgaattctc cacaccaagc acgtactgtg    6060
ttttttggca gttttttgac agttaagaaa tccattctta catctgatgg gactgtaatg    6120
cctaatgttt tgtcctatgc ggcccagacc tcacggggtt actgtggagc tgcaattgtg    6180
gccgggtctc cggctcgcat tataggcata cattccgctg gaactggctc agttgctttt    6240
tgttctctgg tgtccagaga cgctttggag cggaccctgc tcagaaaca aggaaatgtg     6300
gtccgtttgg atgatgatgt aagagtgtct gttccgcgcc gtaccaaatt ggttaaatca    6360
ttggcctacc ccattttcaa acccgatttt gggccagcac ctctgtccca gtttgacaaa    6420
agattggcag acggcgtgaa acttgatgaa gttgtgtttg ctaagcacac aggagacaag    6480
gagatctctg cacctgacca aaagtggctg ctccgcgcag ctcatgttta tgcccagaaa    6540
gtcttctccc gcattgggtt tgataaccag gcattgaccg aggaggaggc catttgcggc    6600
attcctggac ttgacaaaat ggaacaagac actgctccgg gcttacccta tgcacagcag    6660
aacaagagaa gaaaagacat ttgtgacttt gagaaaggcc agttaaaggg ggctgctaag    6720
ctccagaaag agcggtttct taaggagac tactccgatt tggtctatca atcatttcta     6780
aaggatgaaa ttcggccact tgaaaaagtt agggctggca agaccggct gatcgatgtg     6840
cccccgatgc cccatgtggt tgtcgggcgg caactcctcg gccggtttgt ctccaaattc    6900
cacgaagcaa atggatttga gattggttct gcaataggat gtgaccctga tgtggattgg    6960
actcggtttg gccttgagct cgagcggtat aggtatgttt atgcctgtga ctattctcgg    7020
tttgatgcca accacgctgc tgatgctatg agagttgttc tcaactattt cttctctgag    7080
gaccacgggt tcgaccctgg tgtacccgcc ttcatcgagt ctcttattga ctcggtgcat    7140
gcttatgaag agaagagata taatatttat ggaggtttac cctctgggtg ttcttgcacc    7200
tcaattttga atactgtttt gaataatgtt tacattcttg cagcaatgat gaaggctttt    7260
gaaaattttg agcctgatga tattttggtt ttatgctatg gggatgattg cctcatagcc    7320
tctgatttgg aaattgattt tcagaaactt gtccctgtct ttgcagattt tgggcaagtt    7380
attactactg ctgacaagac tgactttttt aaacttacca cgctttctga ggttactttt    7440
ttgaagcgtg ctttgttcc tgacggggcg ctttacaagc cagttatgga tgtgaagacc     7500
ctggaagcaa tcctcagttt cgttcgccct ggtacacagg ctgagaagct cctctctgtt    7560
gcgcagttgg ccgccactg cgaaccggat gagtatgagc acctgtttca gccgtttgag    7620
gggatgtatt acgtccctac ttggcgtgac ttgcgcctcc agtggttgat gaagcttgga    7680
```

-continued

```
tgctaaactt tttttggtt tgtttttct tgttttttct tttaatctgt agagttaaga      7740 ttttagatt aagagttttt tggaattaga taagagttta gtgagtagtt ttgagcaaaa      7800 aaaaaaaaa aaaaaaaaaa aaaaaaaaaa aaaaaaaaa                             7839
```

<210> SEQ ID NO 3
<211> LENGTH: 2248
<212> TYPE: PRT
<213> ORGANISM: Equine rhinitis A virus

<400> SEQUENCE: 3

```
Met Met Ala Ala Ser Lys Val Tyr Arg Val Cys Glu Gln Thr Leu Leu
1               5                   10                  15

Ala Gly Ala Val Arg Met Met Asp Lys Phe Leu Gln Lys Arg Val Val
                20                  25                  30

Phe Val Pro His Leu Asp Lys Gln Val Arg Leu Thr Gly Leu His Asn
            35                  40                  45

Tyr Asp Asn Thr Cys Trp Leu Asn Ala Leu Thr Gln Leu Thr Gln Ile
50                  55                  60

Leu Gly Ile Arg Leu Phe Asp Glu His Phe Gly Asn Arg Gly Leu Phe
65                  70                  75                  80

Thr Arg Lys Thr Ile Asp Trp Val Ser Asp Gln Thr Gly Ile Lys Asp
                85                  90                  95

Leu Lys Ser Gly Ala Pro Pro Leu Val Val Tyr Lys Leu Trp Gln
            100                 105                 110

His Gly His Leu Asp Val Gly Thr Met Glu Lys Pro Arg Pro Ile Thr
        115                 120                 125

Leu Trp Ser Gly Pro Lys Val Cys Leu Ser Asp Met Trp Ala Cys Val
130                 135                 140

Ser Ala Lys Pro Gly His Ala Val Phe Tyr Leu Leu Thr Asp Glu Gly
145                 150                 155                 160

Trp Ile Cys Ile Asp Asp Lys Lys Ile Tyr Tyr Glu Thr Pro Glu Pro
                165                 170                 175

Asp Asp Val Leu Val Phe Ala Pro Tyr Asp Phe Glu Ser Leu Gly Lys
            180                 185                 190

Asp Pro Pro Arg Leu His Gln Arg Tyr Glu Lys Ala Phe Lys Lys Leu
        195                 200                 205

Ser Gly Ala Gly Thr Ser Thr Pro Thr Thr Gly Asn Gln Asn Met Ser
210                 215                 220

Gly Asn Ser Gly Ser Ile Val Gln Asn Phe Tyr Met Gln Gln Tyr Gln
225                 230                 235                 240

Asn Ser Ile Asp Ala Asp Leu Gly Asp Asn Val Ile Ser Pro Glu Gly
                245                 250                 255

Gln Gly Ser Asn Thr Ser Ser Ser Thr Ser Ser Ser Gln Ser Ser Gly
            260                 265                 270

Leu Gly Gly Trp Phe Ser Ser Leu Leu Asn Leu Gly Thr Lys Leu Leu
        275                 280                 285

Ala Asp Lys Lys Thr Glu Glu Thr Thr Asn Ile Glu Asp Arg Ile Glu
290                 295                 300

Thr Thr Val Val Gly Val Thr Ile Ile Asn Ser Gln Gly Ser Val Gly
305                 310                 315                 320

Thr Thr Tyr Cys Tyr Ser Lys Pro Asp Ser Lys Ala Pro Ser Thr Val
                325                 330                 335

Ser Asp Pro Val Thr Arg Leu Gly Pro Thr Leu Ser Arg His Tyr Thr
            340                 345                 350
```

-continued

Phe Lys Val Gly Glu Trp Pro His Ser Gln Ser His Gly His Ala Trp
        355                 360                 365
Ile Cys Pro Leu Pro Gly Asp Lys Leu Lys Lys Met Gly Ser Phe His
    370                 375                 380
Glu Val Val Lys Ala His His Leu Val Lys Asn Gly Trp Asp Val Val
385                 390                 395                 400
Val Gln Val Asn Ala Ser Phe Ala His Ser Gly Ala Leu Cys Val Ala
                405                 410                 415
Ala Val Pro Glu Tyr Glu His Thr His Glu Lys Ala Leu Lys Trp Ser
            420                 425                 430
Glu Leu Glu Glu Pro Ala Tyr Thr Tyr Gln Gln Leu Ser Val Phe Pro
        435                 440                 445
His Gln Leu Leu Asn Leu Arg Thr Asn Ser Ser Val His Leu Val Met
    450                 455                 460
Pro Tyr Ile Gly Pro Gly Pro Thr Thr Asn Leu Thr Leu His Asn Pro
465                 470                 475                 480
Trp Thr Ile Val Ile Leu Ile Leu Ser Glu Leu Thr Gly Pro Gly Gln
                485                 490                 495
Thr Val Pro Val Thr Met Ser Val Ala Pro Ile Asp Ala Met Val Asn
            500                 505                 510
Gly Pro Leu Pro Asn Pro Glu Ala Pro Ile Arg Val Val Ser Val Pro
        515                 520                 525
Glu Ser Asp Ser Phe Met Ser Ser Val Pro Asp Asn Ser Thr Pro Leu
    530                 535                 540
Tyr Pro Lys Val Val Val Pro Pro Arg Gln Val Pro Gly Arg Phe Thr
545                 550                 555                 560
Asn Phe Ile Asp Val Ala Lys Gln Thr Tyr Ser Phe Cys Ser Ile Ser
                565                 570                 575
Gly Lys Pro Tyr Phe Glu Val Thr Asn Thr Ser Gly Asp Glu Pro Leu
            580                 585                 590
Phe Gln Met Asp Val Ser Leu Ser Ala Ala Glu Leu His Gly Thr Tyr
        595                 600                 605
Val Ala Ser Leu Ser Ser Phe Phe Ala Gln Tyr Arg Gly Ser Leu Asn
    610                 615                 620
Phe Asn Phe Ile Phe Thr Gly Ala Ala Ala Thr Lys Ala Lys Phe Leu
625                 630                 635                 640
Val Ala Phe Val Pro Pro His Thr Ala Ala Pro Lys Thr Arg Asp Glu
                645                 650                 655
Ala Met Ala Cys Ile His Ala Val Trp Asp Val Gly Leu Asn Ser Ala
            660                 665                 670
Phe Ser Phe Asn Val Pro Tyr Ser Ser Pro Ala Asp Phe Met Ala Val
        675                 680                 685
Tyr Ser Ala Glu Ala Thr Val Val Asn Val Ser Gly Trp Leu Gln Val
    690                 695                 700
Tyr Ala Leu Thr Ala Leu Thr Ser Thr Asp Ile Ala Val Asn Ser Lys
705                 710                 715                 720
Gly Arg Val Leu Val Ala Val Ser Ala Gly Pro Asp Phe Ser Leu Arg
                725                 730                 735
His Pro Val Asp Leu Pro Asp Lys Gln Val Thr Asn Val Gly Glu Asp
            740                 745                 750
Gly Glu Pro Gly Glu Thr Glu Pro Arg Tyr Ala Leu Ser Pro Val Asp
        755                 760                 765

```
Met His Val His Thr Asp Val Ser Phe Leu Leu Asp Arg Phe Phe Asp
770                 775                 780

Val Glu Thr Ile Glu Leu Ser Asn Leu Thr Gly Ser Pro Thr Thr His
785                 790                 795                 800

Ile Leu Asn Pro Phe Gly Ser Thr Ala Gln Leu Ala Trp Ala Arg Leu
                805                 810                 815

Leu Asn Thr Cys Thr Tyr Phe Phe Ser Asn Leu Glu Leu Ser Ile Gln
                820                 825                 830

Phe Lys Phe Thr Thr Met Pro Ser Ser Val Glu Lys Gly Phe Val Trp
            835                 840                 845

Val Lys Trp Phe Pro Val Gly Ala Pro Thr Lys Thr Thr Asp Ala Trp
850                 855                 860

Gln Leu Glu Gly Gly Gly Asn Ser Val Arg Ile Gln Lys Leu Ala Val
865                 870                 875                 880

Ala Gly Leu Ser Pro Thr Val Ile Phe Lys Ile Ala Gly Ser Arg Ser
                885                 890                 895

Gln Ala Cys Gly Phe Asn Val Pro Tyr Thr Ser Met Trp Arg Val Val
            900                 905                 910

Pro Val Phe Tyr Asn Gly Trp Gly Ala Pro Thr Lys Glu Lys Ala Thr
        915                 920                 925

Tyr Asn Trp Leu Pro Gly Ala His Phe Gly Ser Ile Leu Leu Thr Ser
930                 935                 940

Asp Ala His Asp Lys Gly Gly Cys Tyr Leu Arg Tyr Arg Phe Pro Arg
945                 950                 955                 960

Ala Ser Met Tyr Cys Pro Arg Pro Ile Pro Pro Ala Phe Thr Arg Pro
                965                 970                 975

Ala Asp Lys Thr Arg His Lys Phe Pro Thr Asn Ile Asn Lys Gln Cys
            980                 985                 990

Thr Asn Tyr Ala Leu Leu Lys Leu Ala Gly Asp Val Glu Ser Asn Pro
        995                 1000                1005

Gly Pro Thr Ile Phe Ser Lys Ala Ser Ala Asp Leu Asn Ala Leu
    1010                1015                1020

Ser Thr Ser Leu Gly Glu Leu Thr Gly Met Leu Lys Asp Leu Lys
    1025                1030                1035

Ala Lys Ala Glu Thr Tyr Ser Pro Phe Tyr Lys Met Ala Lys Met
    1040                1045                1050

Leu Phe Lys Leu Ala Thr Leu Ala Val Ala Ala Met Arg Thr Lys
    1055                1060                1065

Asp Pro Val Val Val Val Met Leu Ile Ala Asp Phe Gly Leu Glu
    1070                1075                1080

Val Phe Asp Thr Gly Phe Phe Ser Tyr Phe Gln Glu Lys Leu
    1085                1090                1095

Gln Pro Tyr Met Lys Thr Ile Pro Gly Lys Val Ser Asp Leu Val
    1100                1105                1110

Thr Asp Ala Ala Thr Ala Ala Gln Ile Pro Lys Gly Val Tyr
    1115                1120                1125

Ser Phe Val Ser Ser Phe Glu Thr Pro Glu Gly Val Val Glu
    1130                1135                1140

Lys Gln Val Ser Leu Arg Thr Ile Asn Asp Ile Phe Thr Leu Leu
    1145                1150                1155

Lys Asn Ser Asp Trp Phe Ile Lys Thr Leu Val Ala Leu Lys Lys
    1160                1165                1170

Trp Leu Val Ser Trp Phe Lys Gln Glu Gln Gln Ala Asp Asp Ala
```

```
                1175                1180               1185

Leu Tyr Ser Glu Leu Glu Lys Tyr Pro Leu Tyr Lys Leu Lys Leu
    1190                1195                    1200

Lys Glu Pro Asp Thr Gln Glu Glu Ala Arg Gln Trp Phe Lys Asp
    1205                1210                    1215

Met Gln Gln Arg Ala Leu Ala Val Lys Asp Lys Gly Leu Phe Ser
    1220                1225                    1230

Leu Leu Gln Ile Pro Leu Val Asn Leu Pro Thr Ser Arg Pro Glu
    1235                1240                    1245

Pro Val Val Cys Val Leu Arg Gly Ala Ser Gly Gln Gly Lys Ser
    1250                1255                    1260

Tyr Leu Ala Asn Met Met Ala Gln Ala Ile Ser Leu Leu Leu Thr
    1265                1270                    1275

Gly Lys Gln Asn Ser Val Trp Ser Cys Pro Pro Asp Pro Thr Tyr
    1280                1285                    1290

Phe Asp Gly Tyr Asn Gly Gln Ala Val Val Ile Met Asp Asp Leu
    1295                1300                    1305

Gly Gln Asn Pro Asn Gly Ala Asp Phe Lys Tyr Phe Cys Gln Met
    1310                1315                    1320

Val Ser Thr Thr Ala Phe Val Pro Pro Met Ala His Leu Asp Asp
    1325                1330                    1335

Lys Gly Ile Pro Phe Thr Ser Pro Val Val Ile Cys Thr Thr Asn
    1340                1345                    1350

Leu His Ser Ser Phe Thr Pro Ile Thr Val Ser Cys Pro Glu Ala
    1355                1360                    1365

Leu Lys Arg Arg Phe Arg Phe Asp Val Thr Val Ser Ala Lys Pro
    1370                1375                    1380

Gly Phe Val Arg Thr Val Gly Ser Ser Gln Leu Leu Asn Leu Pro
    1385                1390                    1395

Leu Ala Leu Lys Pro Ala Gly Leu Pro Pro His Pro Ile Phe Glu
    1400                1405                    1410

Asn Asp Met Pro Ile Leu Asn Gly Gln Ala Val Lys Leu Ala Leu
    1415                1420                    1425

Ser Gly Val Glu Val Thr Ala Phe Glu Leu Ile Glu Met Ile Leu
    1430                1435                    1440

Ser Glu Val Gln Asn Arg Gln Asp Thr His Lys Met Pro Ile Phe
    1445                1450                    1455

Lys Gln Ser Trp Ser Asp Leu Phe Lys Lys Cys Thr Ser Asp Glu
    1460                1465                    1470

Glu Gln Lys Met Leu Gln Phe Leu Ile Asp His Lys Asp Ser Glu
    1475                1480                    1485

Ile Leu Lys Ala Phe Val Ser Glu Arg Ser Ile Met Leu His Glu
    1490                1495                    1500

Glu Tyr Met Lys Trp Glu Ser Tyr Met Thr Arg Arg Ala Lys Tyr
    1505                1510                    1515

His Arg Leu Ala Ala Asp Phe Ala Met Phe Leu Ser Ile Leu Thr
    1520                1525                    1530

Ser Leu Ile Val Ile Phe Cys Leu Val Tyr Ser Met Tyr Gln Leu
    1535                1540                    1545

Phe Lys Thr Pro Asp Glu His Ser Ala Tyr Asp Pro Ala Thr Lys
    1550                1555                    1560

Pro Lys Pro Lys Thr Gln Glu Ile Lys Thr Leu Lys Ile Arg Thr
    1565                1570                    1575
```

```
Glu Thr Gly Val Pro Ala Thr Asp Leu Gln Gln Ser Val Met Lys
    1580                1585                1590

Asn Val Gln Pro Ile Glu Leu Tyr Cys Glu Gly Asn Leu Val Thr
    1595                1600                1605

Asp Cys Ser Ala Leu Gly Val Tyr Asp Asn Ser Tyr Leu Val Pro
    1610                1615                1620

Leu His Leu Phe Glu Phe Asp Phe Asp Thr Ile Val Leu Gly Gly
    1625                1630                1635

Arg Gln Tyr Ser Lys Ala Asp Cys Glu Lys Val Glu Phe Glu Leu
    1640                1645                1650

Ser Val Gly Gly Asp Met Val Ser Ser Asp Ala Cys Leu Leu Arg
    1655                1660                1665

Leu Pro Ser Gly Pro Lys Val Arg Asn Ile Leu His Leu Phe Thr
    1670                1675                1680

Asn Glu Ile Glu Leu Lys Lys Met Thr Gln Ile Thr Gly Ile Met
    1685                1690                1695

Asn Ser Pro His Gln Ala Arg Thr Val Phe Phe Gly Ser Phe Leu
    1700                1705                1710

Thr Val Lys Lys Ser Ile Leu Thr Ser Asp Gly Thr Val Met Pro
    1715                1720                1725

Asn Val Leu Ser Tyr Ala Ala Gln Thr Ser Arg Gly Tyr Cys Gly
    1730                1735                1740

Ala Ala Ile Val Ala Gly Ser Pro Ala Arg Ile Ile Gly Ile His
    1745                1750                1755

Ser Ala Gly Thr Gly Ser Val Ala Phe Cys Ser Leu Val Ser Arg
    1760                1765                1770

Asp Ala Leu Glu Arg Thr Leu Pro Gln Lys Gln Gly Asn Val Val
    1775                1780                1785

Arg Leu Asp Asp Asp Val Arg Val Ser Val Pro Arg Arg Thr Lys
    1790                1795                1800

Leu Val Lys Ser Leu Ala Tyr Pro Ile Phe Lys Pro Asp Phe Gly
    1805                1810                1815

Pro Ala Pro Leu Ser Gln Phe Asp Lys Arg Leu Ala Asp Gly Val
    1820                1825                1830

Lys Leu Asp Glu Val Val Phe Ala Lys His Thr Gly Asp Lys Glu
    1835                1840                1845

Ile Ser Ala Pro Asp Gln Lys Trp Leu Leu Arg Ala Ala His Val
    1850                1855                1860

Tyr Ala Gln Lys Val Phe Ser Arg Ile Gly Phe Asp Asn Gln Ala
    1865                1870                1875

Leu Thr Glu Glu Glu Ala Ile Cys Gly Ile Pro Gly Leu Asp Lys
    1880                1885                1890

Met Glu Gln Asp Thr Ala Pro Gly Leu Pro Tyr Ala Gln Gln Asn
    1895                1900                1905

Lys Arg Arg Lys Asp Ile Cys Asp Phe Glu Lys Gly Gln Leu Lys
    1910                1915                1920

Gly Ala Ala Lys Leu Gln Lys Glu Arg Phe Leu Lys Gly Asp Tyr
    1925                1930                1935

Ser Asp Leu Val Tyr Gln Ser Phe Leu Lys Asp Glu Ile Arg Pro
    1940                1945                1950

Leu Glu Lys Val Arg Ala Gly Lys Thr Arg Leu Ile Asp Val Pro
    1955                1960                1965
```

Pro Met Pro His Val Val Gly Arg Gln Leu Leu Gly Arg Phe
    1970            1975                1980

Val Ser Lys Phe His Glu Ala Asn Gly Phe Glu Ile Gly Ser Ala
    1985                1990                1995

Ile Gly Cys Asp Pro Asp Val Asp Trp Thr Arg Phe Gly Leu Glu
    2000                2005                2010

Leu Glu Arg Tyr Arg Tyr Val Tyr Ala Cys Asp Tyr Ser Arg Phe
    2015                2020                2025

Asp Ala Asn His Ala Ala Asp Ala Met Arg Val Val Leu Asn Tyr
    2030                2035                2040

Phe Phe Ser Glu Asp His Gly Phe Asp Pro Gly Val Pro Ala Phe
    2045                2050                2055

Ile Glu Ser Leu Ile Asp Ser Val His Ala Tyr Glu Glu Lys Arg
    2060                2065                2070

Tyr Asn Ile Tyr Gly Gly Leu Pro Ser Gly Cys Ser Cys Thr Ser
    2075                2080                2085

Ile Leu Asn Thr Val Leu Asn Asn Val Tyr Ile Leu Ala Ala Met
    2090                2095                2100

Met Lys Ala Phe Glu Asn Phe Glu Pro Asp Asp Ile Leu Val Leu
    2105                2110                2115

Cys Tyr Gly Asp Asp Cys Leu Ile Ala Ser Asp Leu Glu Ile Asp
    2120                2125                2130

Phe Gln Lys Leu Val Pro Val Phe Ala Asp Phe Gly Gln Val Ile
    2135                2140                2145

Thr Thr Ala Asp Lys Thr Asp Phe Phe Lys Leu Thr Thr Leu Ser
    2150                2155                2160

Glu Val Thr Phe Leu Lys Arg Ala Phe Val Pro Asp Gly Ala Leu
    2165                2170                2175

Tyr Lys Pro Val Met Asp Val Lys Thr Leu Glu Ala Ile Leu Ser
    2180                2185                2190

Phe Val Arg Pro Gly Thr Gln Ala Glu Lys Leu Leu Ser Val Ala
    2195                2200                2205

Gln Leu Ala Gly His Cys Glu Pro Asp Glu Tyr Glu His Leu Phe
    2210                2215                2220

Gln Pro Phe Glu Gly Met Tyr Tyr Val Pro Thr Trp Arg Asp Leu
    2225                2230                2235

Arg Leu Gln Trp Leu Met Lys Leu Gly Cys
    2240                2245

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgaatagcaa gggccgtgtt                                              20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 5
accgttgtaa aagactggca ca                                         22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcagtaaaa cgcaacaacc at                                         22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtgaagaat gtcctgaagg ca                                         22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accatccacc taaaccagac ga                                         22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attggctttg tcaggtgttg aa                                         22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtttctaact ttgggacccg aa                                         22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```

```
-continued tggatttgag attggttctg ca                                              22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaacgaaa ctgaggattg                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctgtagcgtc agtaaaacgc                                                 20

<210> SEQ ID NO 14
<211> LENGTH: 340
<212> TYPE: DNA
<213> ORGANISM: Equine rhinitis A virus

<400> SEQUENCE: 14
acttttagga gatgaccaaa cgcagtaacc gcaagcaatt gcctgtagcg tcagtaaaac     60
gcaatacaca agatttgagc ctgtagcgtc agtaaaacgc tgcaaccaca agctattgac    120
tgtagcgtca gtaaaacgca aacattcttg tggcgctcgc gtagcgctca agtgcagagc    180
ttcccggctt taagggttac tgctcgtaat gagagcacat gacattttgc caagatttcc    240
tggcaattgt cacgggagag aggagcccgt tctcgggcac tttctctca aacaatgttg     300 gcgcgcctcg gcgcgccccc ccttttttcag cccctgtca                          340
```